United States Patent
Ngo et al.

(10) Patent No.: US 9,566,442 B2
(45) Date of Patent: Feb. 14, 2017

(54) SYSTEMS AND METHODS FOR USING PULMONARY ARTERY PRESSURE FROM AN IMPLANTABLE SENSOR TO DETECT MITRAL REGURGITATION AND OPTIMIZE PACING DELAYS

(71) Applicant: PACESETTER, INC., Sylmar, CA (US)

(72) Inventors: Thao Ngo, Shakopee, MN (US); Kathleen Kresge, Minneapolis, MN (US); Michael Kane, Pewaukee, WI (US); Scott Patrick Simon, Billings, MT (US)

(73) Assignee: Pacesetter, Inc., Sylmar, CA (US)

( * ) Notice: Subject to any disclaimer, the term of this patent is extended or adjusted under 35 U.S.C. 154(b) by 754 days.

(21) Appl. No.: 13/681,273

(22) Filed: Nov. 19, 2012

(65) Prior Publication Data

US 2014/0142444 A1     May 22, 2014

(51) Int. Cl.
| | |
|---|---|
| *A61N 1/00* | (2006.01) |
| *A61B 5/00* | (2006.01) |
| *A61N 1/365* | (2006.01) |
| *A61B 5/021* | (2006.01) |
| *A61B 5/02* | (2006.01) |

(Continued)

(52) U.S. Cl.
CPC ....... *A61N 1/36564* (2013.01); *A61B 5/02028* (2013.01); *A61B 5/02116* (2013.01); *A61B 5/02152* (2013.01); *A61B 5/0452* (2013.01); *A61B 5/4836* (2013.01);

(Continued)

(58) Field of Classification Search
None
See application file for complete search history.

(56) References Cited

U.S. PATENT DOCUMENTS

| | | | |
|---|---|---|---|
| 4,984,572 A | 1/1991 | Cohen | |
| 4,986,270 A | 1/1991 | Cohen | |

(Continued)

FOREIGN PATENT DOCUMENTS

| | | | |
|---|---|---|---|
| WO | 2007002888 A1 | 1/2007 | |
| WO | 2007078421 A2 | 7/2007 | |

(Continued)

OTHER PUBLICATIONS

Abraham, William T. et al., "Wireless pulmonary artery haemodynamic monitoring in chronic heart failure: a randomised controlled trial," Lancet. 2011;377:658-666.

(Continued)

*Primary Examiner* — Etsub Berhanu

(57) ABSTRACT

Techniques are provided for use with a pulmonary artery pressure (PAP) monitor having an implantable PAP sensor. In one example, a PAP signal is sensed that is representative of beat-by-beat variations in PAP occurring during individual cardiac cycles of the patient. The PAP monitor detects peaks within the PAP signal corresponding to valvular regurgitation within the heart, then detects mitral regurgitation (MR) based on the peaks. In other examples, the PAP monitor optimizes pacing parameters based on the PAP signal and corresponding electrical cardiac signals. Examples are provided where the PAP monitor is an external system and other examples are provided where the PAP monitor is a component of an implantable cardiac rhythm management device.

22 Claims, 17 Drawing Sheets

(51) Int. Cl.
*A61B 5/0215* (2006.01)
*A61B 5/0452* (2006.01)
*A61N 1/362* (2006.01)
*A61N 1/368* (2006.01)

(52) U.S. Cl.
CPC ......... *A61N 1/3627* (2013.01); *A61N 1/3682* (2013.01); *A61N 1/3684* (2013.01)

(56) References Cited

U.S. PATENT DOCUMENTS

| | | | |
|---|---|---|---|
| 5,163,429 | A | 11/1992 | Cohen |
| 6,277,078 | B1 | 8/2001 | Porat et al. |
| 7,139,609 | B1 | 11/2006 | Min et al. |
| 7,147,604 | B1 | 12/2006 | Allen et al. |
| 7,248,925 | B2 | 7/2007 | Bruhns et al. |
| 7,272,436 | B2 | 9/2007 | Gill et al. |
| 7,590,446 | B1 | 9/2009 | Min et al. |
| 7,621,036 | B2 | 11/2009 | Cros et al. |
| 7,632,235 | B1 | 12/2009 | Karicherla et al. |
| 7,666,144 | B2 | 2/2010 | Cohen et al. |
| 7,706,865 | B1 | 4/2010 | Snell |
| 7,751,889 | B1 | 7/2010 | Schecter |
| 7,848,793 | B1 | 12/2010 | Shelchuk et al. |
| 7,909,770 | B2 | 3/2011 | Stern et al. |
| 7,949,394 | B2 | 5/2011 | Salo et al. |
| 7,957,802 | B2 | 6/2011 | Patangay et al. |
| 7,974,687 | B1 | 7/2011 | Farazi et al. |
| 8,021,307 | B2 | 9/2011 | White et al. |
| 8,118,749 | B2 | 2/2012 | White et al. |
| 8,126,552 | B2 | 2/2012 | Min et al. |
| 8,145,311 | B2 | 3/2012 | Min |
| 8,249,707 | B2 | 8/2012 | Nabutovsky et al. |
| 8,265,755 | B2 | 9/2012 | Min |
| 2002/0049478 | A1* | 4/2002 | Ding et al. ................. 607/17 |
| 2002/0188329 | A1* | 12/2002 | Struble ........................ 607/23 |
| 2004/0215252 | A1* | 10/2004 | Verbeek et al. ............... 607/9 |
| 2004/0220637 | A1* | 11/2004 | Zdeblick et al. ............. 607/17 |
| 2005/0010257 | A1* | 1/2005 | Lincoln ............... A61B 5/0464 607/14 |
| 2006/0047205 | A1 | 3/2006 | Ludomirsky et al. |
| 2006/0116590 | A1* | 6/2006 | Fayram et al. ............. 600/508 |
| 2006/0200030 | A1 | 9/2006 | White et al. |
| 2006/0224196 | A1* | 10/2006 | Hettrick et al. ................ 607/9 |
| 2006/0283007 | A1 | 12/2006 | Cros et al. |
| 2006/0287602 | A1 | 12/2006 | O'Brien et al. |
| 2006/0287700 | A1 | 12/2006 | White et al. |
| 2007/0197921 | A1 | 8/2007 | Cohen et al. |
| 2008/0033527 | A1* | 2/2008 | Nunez et al. ................ 623/1.13 |
| 2008/0288013 | A1 | 11/2008 | Schecter |
| 2009/0024042 | A1* | 1/2009 | Nunez et al. ................ 600/486 |
| 2009/0054945 | A1 | 2/2009 | Patangay et al. |
| 2009/0118783 | A1 | 5/2009 | Patangay et al. |
| 2009/0299423 | A1 | 12/2009 | Min |
| 2010/0057155 | A1* | 3/2010 | Farazi et al. ................... 607/17 |
| 2010/0094144 | A1 | 4/2010 | Doron |
| 2010/0099993 | A1 | 4/2010 | Cohen et al. |
| 2010/0114228 | A1 | 5/2010 | Bharmi et al. |
| 2010/0130873 | A1* | 5/2010 | Yuen ...................... A61B 5/0205 600/484 |
| 2010/0160794 | A1* | 6/2010 | Banet ................. A61B 5/02125 600/485 |
| 2011/0022112 | A1 | 1/2011 | Min |
| 2011/0029034 | A1* | 2/2011 | Fischer et al. ................ 607/17 |
| 2011/0066055 | A1 | 3/2011 | Bharmi et al. |
| 2012/0065524 | A1* | 3/2012 | Morren ................ A61B 5/1102 600/484 |
| 2012/0136406 | A1 | 5/2012 | Min |
| 2012/0158079 | A1 | 6/2012 | Rosenberg et al. |
| 2012/0165892 | A1 | 6/2012 | Min et al. |
| 2012/0184859 | A1* | 7/2012 | Shah et al. ................... 600/486 |

FOREIGN PATENT DOCUMENTS

| | | |
|---|---|---|
| WO | 2007133873 A2 | 11/2007 |
| WO | 2007078421 A3 | 12/2007 |
| WO | 2007133873 A3 | 1/2008 |
| WO | 2009025667 A1 | 2/2009 |
| WO | 2009025734 A1 | 2/2009 |
| WO | 2010042291 A1 | 4/2010 |
| WO | 2010059291 A1 | 5/2010 |

OTHER PUBLICATIONS

Furberg, Curt D. MD, PhD et al., "Prevalence of Atrial Fibrillation in Elderly Subjects (the Cardiovascular Health Study)," Am J Cardiol. 1994;74:236-241.

Kannel, William B. MD et al., "Epidemiologic Features of Chronic Atrial Fibrillation," N Eng J Med. 1982;306:1018-1022.

Mark, Jonathan B. MD, Atlas of Cardiovascular Monitoring. New York, Churchill Livingstone. 1998: Fig 17.11.

St. Jude Medical LAPTOP-HF Newsletter. Issue No. 2, vol. 2, Jun. 15, 2012, 7 pages.

* cited by examiner

— 1 —

SYSTEMS AND METHODS FOR USING PULMONARY ARTERY PRESSURE FROM AN IMPLANTABLE SENSOR TO DETECT MITRAL REGURGITATION AND OPTIMIZE PACING DELAYS

CROSS REFERENCE TO RELATED APPLICATIONS

This application is related to U.S. patent application Ser. No. 13/681,241, filed concurrently herewith, titled "Systems and Methods for Exploiting Pulmonary Artery Pressure Obtained from an Implantable Sensor to Detect Cardiac Rhythm Irregularities".

FIELD OF THE INVENTION

The invention generally relates to implantable medical devices such as pacemakers and external systems for use therewith and, in particular, to techniques for detecting and tracking mitral regurgitation and for optimizing pacing parameters, particularly for use within patients with heart failure.

BACKGROUND OF THE INVENTION

Heart failure (HF) is a debilitating disease in which abnormal function of the heart leads in the direction of inadequate blood flow to fulfill the needs of the tissues and organs of the body. Typically, the heart loses propulsive power because the cardiac muscle loses capacity to stretch and contract. Often, the ventricles do not adequately eject or fill with blood between heartbeats and the valves regulating blood flow become leaky, allowing regurgitation or backflow of blood. The impairment of arterial circulation deprives vital organs of oxygen and nutrients. Fatigue, weakness and the inability to carry out daily tasks may result. Not all HF patients suffer debilitating symptoms immediately. Some may live actively for years. Yet, with few exceptions, the disease is relentlessly progressive. As HF progresses, it tends to become increasingly difficult to manage. Even the compensatory responses it triggers in the body may themselves eventually complicate the clinical prognosis. For example, when the heart attempts to compensate for reduced cardiac output, it can add muscle causing the ventricles (particularly the left ventricle) to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output, resulting in elevated pressures within the left atrium. Elevated left atrial pressure (LAP) can then exacerbate the HF, particularly congestive HF where the weak pumping of the heart leads to a build-up of fluids in the lungs and other organs and tissues. Often, a progression of HF and the build-up of congestive fluids results in the patient being hospitalized.

Despite current therapies, the rate of HF hospitalizations remains high—about 1.1 million HF hospitalizations annually. A new approach to managing patients has exploited chronic measurements of pulmonary arterial pressures. Pulmonary artery pressure (PAP) is generated by the right ventricle (RV) ejecting blood into the pulmonary circulation, which acts as a resistance to the output from the RV. With each ejection of blood during ventricular systole, pulmonary arterial blood volume increases which stretches the wall of the artery. As the heart relaxes, blood continues to flow from the pulmonary artery into the pulmonary circulation. The smaller arteries and arterioles serve as the chief resistance vessels, and through changes in their diameter, regulate pulmonary vascular resistance. In the recent CHAMPION study, the use of a wireless implantable PAP sensor showed a 30% percent reduction in HF hospitalizations in six months in New York Heart Association (NYHA) Class III HF patients in a prospective, multi-center, randomized (1:1) controlled single blinded clinical trial (n=553). (See, Abraham et al., "Wireless pulmonary artery haemodynamic monitoring in chronic heart failure: a randomised controlled trial," Lancet 2011; 377:658-666). Use of daily PAP measurements allowed physicians to proactively monitor and tailor the patient's pharmacological therapy. Note that the CHAMPION study was directed to the use of a PAP sensor provided by CardioMEMS, Inc., which operates in conjunction with an external PAP monitor. Briefly, the PAP sensor is implanted within the pulmonary artery of the patient using a catheter. Thereafter, once per day (or at some other periodic interval), the patient places an interface device over his or her chest, which receives PAP data wirelessly from the implanted sensor for routing to a clinician for review.

One technique to address HF is cardiac resynchronization therapy (CRT), which is a pacing technique directed to improving cardiac performance by synchronizing the ventricles. Currently, however, CRT has an estimated 25-30% non-responder rate. Some CRT optimization options are currently available for improving CRT efficacy, such as echocardiography and electrical optimization. However, logistical challenges in echocardiographic optimization make it difficult to incorporate the techniques into common clinical practice and more so for follow-up optimization as cardiac reverse remodeling occurs. In addition, electrical optimization also has its limitations in patients with a marked electromechanical delay. Accordingly, it would be desirable to provide improved CRT optimization techniques. In particular, it would be desirable to exploit beat-by-beat PAP measurements for hemodynamic optimization of CRT therapy as such would provide for real-time assessment of current hemodynamic function within the patient to allow the physician to monitor as well as optimize therapy based on PAP. Hence, some aspects of the present invention are directed to CRT optimization techniques that exploit PAP sensor values.

Mitral regurgitation (MR) is a common finding in patients with left ventricular systolic dysfunction (an aspect of HF) and has been established as an independent predictor of mortality. Indeed, it is estimated that 50% of HF patients have MR, which is a disorder of the heart in which the mitral valve (which separates the left atrium (LA) from the left ventricle (LV)) fails to close properly when the LV pumps blood. The presence of any degree of MR in patients with LV dysfunction is associated with reduced survival. Moreover, the worse the MR, the worse the prognosis. Note that, in patients with MR it has been found that retrograde pressure jets arising due to MR are reflected in the PAP waveform. Accordingly, it would be desirable to provide techniques for exploiting beat-by-beat PAP measurements to detect and track MR and some aspects of the invention are directed to these ends. Such techniques could be exploited within external PAP monitors of the type used in the CHAMPION study or within implantable cardiac rhythm management devices (CRMDs) such as pacemakers, CRTs or implantable cardioverter-defibrillators (ICDs) or within independent non-wireless PAP measurement systems to leverage more frequent or continuous monitoring of pressures as well as data storage/analysis storage.

SUMMARY OF THE INVENTION

In a first embodiment, systems and methods are provided for use with a medical system having a PAP sensor for implant within a patient for use in detecting and tracking MR. A time-varying PAP signal is sensed that is representative of variations in PAP occurring during individual cardiac cycles of the patient (i.e. the signal includes pulsatile variations due to the beating of the chambers of the heart.) The system detects regurgitation peaks, if present, within the PAP signal representative of retrograde pressure jets from the LV to the LA. The system then detects MR in the patient based on the presence of regurgitation peaks in the PAP signal. In this regard, MR jets are detectable in PAP signals since the pulmonary artery and the lungs effectively act as a fluid filled pressure manometer coupled to the LA. In the presence of MR, a systolic pressure jet thus affects the PAP waveform (via pressure transfer through the lungs) and is reflected as a corresponding peak in the PAP signal.

In one embodiment, the system comprises an external PAP monitor for use with an implantable PAP sensor, wherein the analysis of the PAP signal is performed by the external monitor (or by other external systems) based on PAP data received from the implanted sensor (wirelessly or otherwise.) Hence, a relatively simple and inexpensive PAP monitor can be equipped to detect MR while also collecting and recording pulsatile PAP data to assist the clinician in managing the patient. Additionally or alternatively, PAP-based MR detection methods may be exploited by CRMDs equipped with PAP sensors. For CRMD-based implementations, the methods described herein can be used to detect MR using PAP or to corroborate detection of MR made using heart sounds or other parameters, while also providing useful PAP diagnostic information for subsequent clinician review to aid in the management of HF or other conditions.

In one example, to detect MR the system analyzes PAP signals to determine a rate of change of the PAP signal with time (dPAP/dt), then detects a systolic maximum in the dPAP/dt signal (dPAP/dt|max) and a diastolic minimum in the dPAP/dt signal (dPAP/dt|min) within the PAP waveform corresponding to an individual cardiac cycle. The system examines the dPAP/dt signal within a window between dPAP/dt|max and dPAP/dt|min to detect an MR peak. If MR peaks are found within the PAP waveforms, this is an indication of MR within the patient and suitable warnings or alerts are generated. Assuming MR is indicated, the system then tracks its progression by periodically measuring the amplitude of the MR peaks (such as once per day) to detect any increase in time in peak amplitude indicative of progression of MR. Information pertaining to progression of MR may be used to assess potentially worsening HF.

In a second exemplary embodiment, primarily intended for use with a CRMD, systems and methods are provided for optimizing atrioventricular (AV) and interventricular (VV) pacing delays such as for use in controlling CRT. The CRMD detects a time-varying PAP signal representative of variations in PAP occurring during individual cardiac cycles of the patient and then detects the closure of the AV valves within the PAP signal by, for example, detecting a pulmonary artery diastole (PAD) point within the PAP signal that marks the onset of a new PAP waveform. The CRMD also detects a ventricular depolarization (R-wave) event within the same cardiac cycle by examining an intracardiac electrogram (IEGM). The interval between the closure of AV valves and the peak of the R-wave (herein DeltaTime1) is measured and then the CRMD sets the AV delay to ensure the AV valves close before the R-wave occurs (to ensure that the appropriate atrial kick has completed and the ventricular chamber does not eject against an open AV valve.) This may be achieved by iteratively adjusting the AV delay until DeltaTime1 is within a predetermined acceptable range. Once the AV delay has been set, the CRMD then sets the VV pacing delay based on an interval (herein DeltaTime2) between a pulmonary artery systole (PAS) peak and an MR peak. To this end, the CRMD may iteratively adjust the VV pacing delay until DeltaTime2 is within a predetermined acceptable range while holding the AV delay constant.

Further adjustments to the AV and VV pacing delays may be made to improve cardiac output (CO) based on a hemodynamic optimization performed during a period of time while pulmonary vascular resistance (PVR) is substantially constant within the patient. In this regard, CO can be estimated based on the difference between maximum PAP and pulmonary artery diastole (PAD) pressure using CO=(maxPAP−PAD)/PVR. Hence, assuming PVR is substantially constant (which is true if the measurements of maxPAP and PAD are made at about the same time), CO is thereby proportional to maxPAP−PAD. The CRMD iteratively adjusts pacing delays to increase the difference between maxPAP and PAD to thus increase CO and stroke volume (SV.) Additionally or alternatively, pacing vectors used for delivery of pacing stimulation can be selected or adjusted in attempt to improve CO, particularly if the CRMD is equipped with a multi-pole LV lead as in many CRT devices. For example, in combination devices (i.e. PAP and CRMD equipped), this optimization may be performed automatically. Still further, pacing delay values or pacing vectors can be selected or adjusted based on the filling and emptying of the RV and the LA as assessed using the PAP signal. To this end, the CRMD divides the PAP waveform corresponding to a cardiac cycle into an RV systolic emptying portion and an LA diastolic filling portion by detecting a dicrotic notch, which represents aortic and pulmonic valve closure and the end of systole. The slope of the RV systolic emptying portion of the PAP waveform and the slope of the LA diastolic filling portion of the PAP waveform are both measured and then pacing parameters are adjusted to optimize the slopes. The relative intervals of these portions can also be exploited. In still other examples, the area under curve within the RV systolic emptying portion of the PAP waveform and the area under curve within the LA diastolic filling portion of the PAP waveform are both measured and used to adjust pacing parameters. If a CRMD has not yet been implanted within the patient, the hemodynamic assessment and optimization techniques described herein can be used to guide implant of pacing leads at optimal locations.

In some examples, the CRMD or the external PAP monitoring system also exploits LAP signal data, which may be obtained from an LAP sensor (if provided) or may be derived from the PAP signal. In this regard, it has been found that PAP signals obtained from the aforementioned PAP sensors are strongly correlated to LAP with the main difference being the gradient across the lungs and pulmonary veins. Accordingly, the methods summarized above are modified where appropriate to exploit atrial and ventricular components of an LAP waveform for MR detection and hemodynamic optimization. For timing optimization, the capability to monitor both the atrial and ventricular portions of the LAP waveform allows for optimization of the area under the atrial portion of the curve to ensure that atrial kick is not truncated by a premature ventricular contraction (PVC) or premature ventricular activation. Also, the system may leverage IEGMs sensed at the sensor lead to differentiate atrial and ventricular mechanical LAP components when paired with atrial activation, or the device may examine dLAP/dt|min to differentiate atrial and ventricular components. In this regard, the atrial component should be slower than the ventricular component when compared to ventricular relaxation because of muscle mass.

Thus, techniques are provided that provide, inter alia, for (a) the chronic detection, monitoring and alerting of MR presence and progression using a PAP waveform, (b) the collection and analysis of PAP hemodynamic data for AV and VV pacing delay optimization; and (c) the hemodynamic optimization of CRT using the PAP waveform. Hence, aspects of the invention are broadly directed to providing techniques for use within a wide variety of waveform devices (with or without an EGM). There is a large population of patients that will not receive a CRM device but may receive a PAP or similar device. System and method implementations of these and other techniques are presented herein.

BRIEF DESCRIPTION OF THE DRAWINGS

Features and advantages of the described implementations can be more readily understood by reference to the following description taken in conjunction with the accompanying drawings.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of PAP Monitoring Systems

Figure 1:
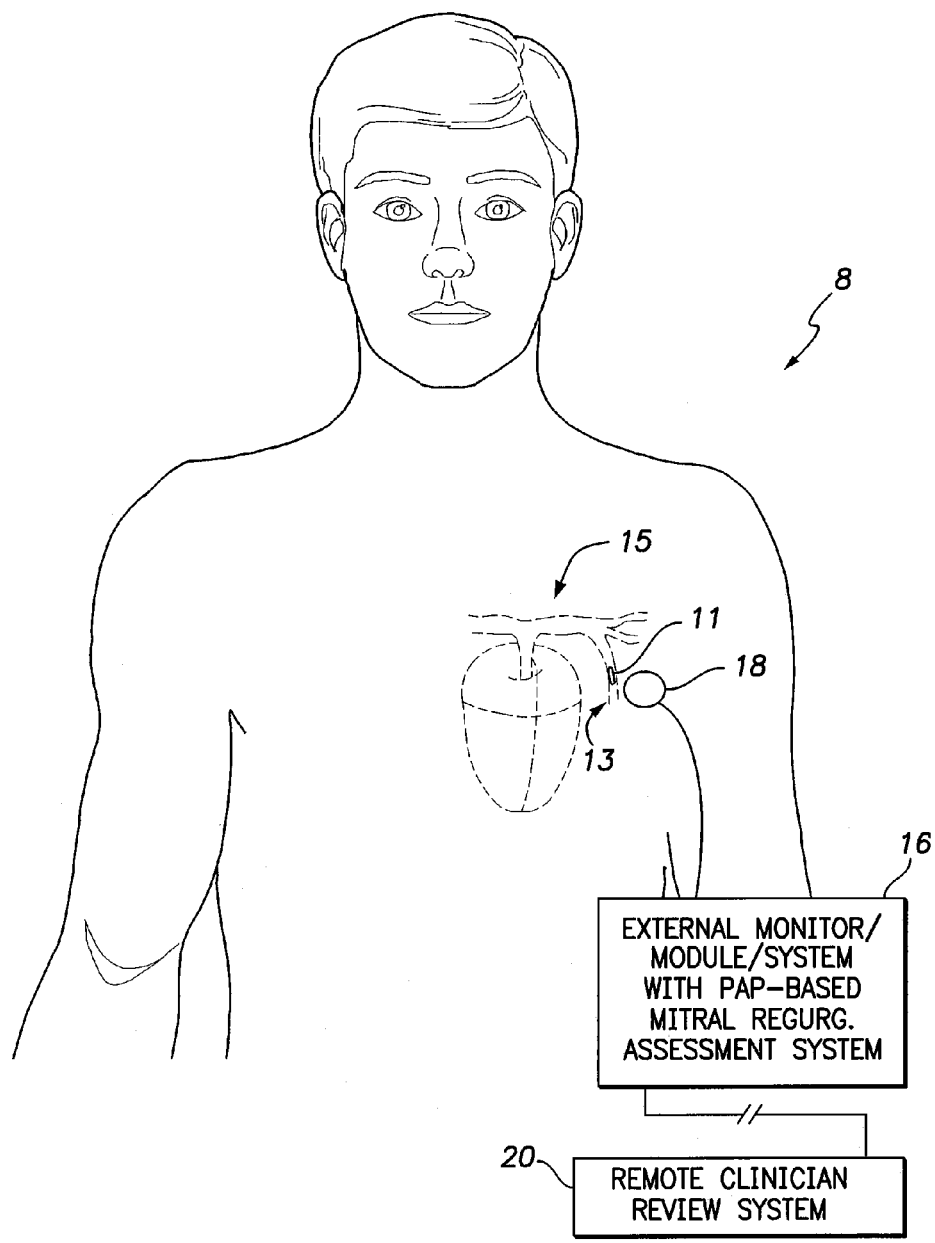
FIG. 1 illustrates a first exemplary PAP monitoring system having an external monitor equipped to detect MR based on PAP signals received from an implantable sensor.

FIG. 1 illustrates a first exemplary PAP monitoring system 8 equipped with a PAP sensor 11 implanted within one of the branches 13 of the pulmonary artery 15 for use with an external monitor, module or system 16. The external system receives signals from the PAP sensor for analysis to detect and track MR within the patient and to provide PAP-based diagnostic data such as PAP waveforms. To power the sensor and to retrieve data therefrom, the patient or caregiver places a wand 18 over the chest to deliver power to the implanted sensor via electromagnetic induction and receives wireless signals from a pressure transducer within the sensor for analysis. Then, external system 16 analyzes the PAP signals to detect MR and forwards the results to a remote clinician review system 20 for display. Note that external system 16 can comprise multiple components. For example, the system may include a bedside module for receiving PAP signals from wand 18 and a centralized processing system at a remote location that receives the PAP signals from the bedside module for analysis. The centralized system then forwards the results of its analysis to the clinician review system. In other implementations, the clinician review system instead performs the analysis based on PAP data it receives from system 16. In at least some embodiments, centralized computing systems such as the HouseCall™ system or the Merlin@home—Merlin.Net systems of St. Jude Medical may be used to relay or process at least some of the data. Parameters collected by the PAP monitor may thereby be used to assess or monitor multiple aspects of cardiac performance and overall disease progression in the absence of an IEGM for patients who lack an implantable CRMD.

Exemplary PAP sensors for use as sensor 11 are discussed in U.S. Pat. Nos. 7,621,036; 7,147,604; 8,021,307; 8,118,749; and 7,909,770, each initially assigned to CardioMems, Inc. See, also, the following published patent applications of CardioMems: 2006/0200030; 2006/0283007; 2006/0287602 and 2006/0287700. Note that FIG. 1 provides a stylized representation of the PAP sensor, the heart and the pulmonary artery vasculature to illustrate pertinent features of this exemplary embodiment of the invention. The actual shape and location of the PAP sensor may differ. Also, the figure is not intended to be anatomically accurate and, in particular, does not show the tissues connecting the base of the pulmonary artery to the RV via the mitral valve. A more accurate illustration of the heart and portions of the pulmonary artery is provided within FIG. 15, discussed below. Note also that wireless systems are not necessarily used. The system can instead exploit a lead-like sensor with a device (CRM or non-CRM) generating the power and performing the analysis.

Figure 2:
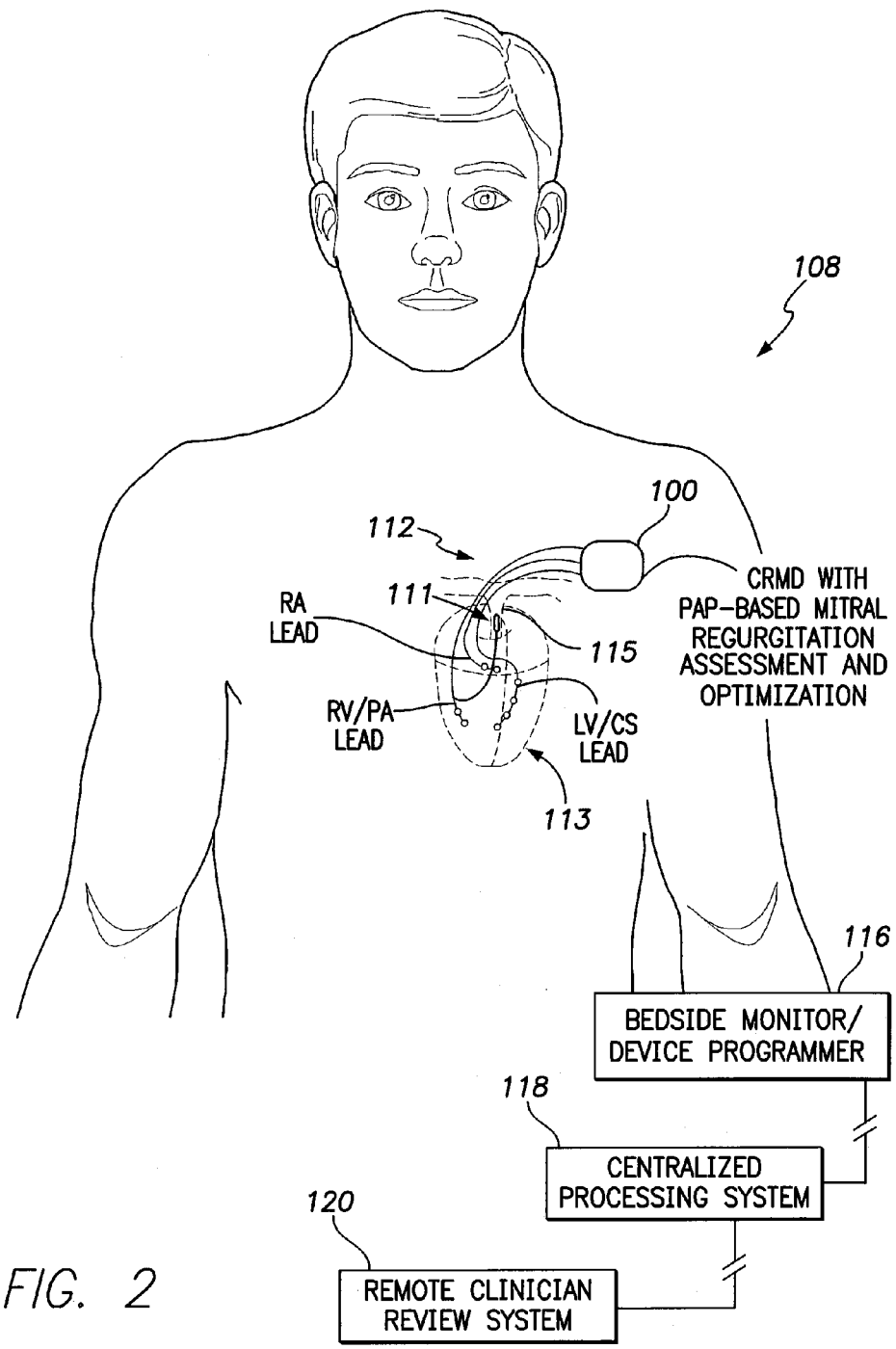
FIG. 2 illustrates a second exemplary PAP monitoring system wherein a CRMD is equipped to detect MR based on PAP signals and further equipped to optimize pacing parameters using the PAP signal.

FIG. 2 illustrates a second exemplary system 108, which is equipped with a PAP sensor 111 implanted within the pulmonary artery 115 for use with a CRMD 100. The CRMD may be, for example, a pacemaker, CRT device, ICD or other any suitably-equipped implantable medical device. In addition to performing cardiac rhythm management functions, CRMD 100 receives signals from the PAP sensor for analysis to detect MR and to optimize pacing parameters based, at least in part, on the PAP waveforms. In this particular example, the PAP sensor is installed via an RV/PA lead, which includes a lead extension for positioning the sensor in the pulmonary artery. An example of this type of lead is described in U.S. Pat. No. 7,632,235 to Karicherla et al. Additional leads 112 are implanted on or within the heart of the patient, including a multi-pole LV lead implanted via the coronary sinus (CS). In the example shown, the LV lead is a quad-pole lea (such as the Quartet™ lead provided by St Jude Medical) have a set of four electrodes 113 providing for a variety of programmable pacing vector combinations. An exemplary RA lead is also shown. Both the RA and RV leads are bipolar leads with tip/ring electrode pairs. The various leads may also include coil electrodes as well as additional physiological sensors besides the PAP sensor. See FIG. 15, described below, for a more complete illustration an exemplary lead system.

If MR is detected or if a problem arises in optimizing pacing parameters, the CRMD can issue warning signals. The warning signals may be generated to alert the patient using an internal warning device (which is part of the CRMD) or may be forwarded to an external device 116 such as a bedside monitor. The internal warning device may be a vibrating device, audible device, or a "tickle" voltage device that, in either case, provides perceptible stimulation to the patient to alert the patient to consult a clinician or other caregiver. In one example, once the warning is felt, the patient positions a handheld device above his or her chest. The handheld device, which might be a personal advisory module (PAM), receives short-range telemetry signals from the implanted device and provides audible or visual verification of the warning signal. The handheld warning device thereby provides confirmation of the warning to the patient, who might otherwise be uncertain as to the reason for the internally generated warning signal. For further information regarding this type of warning/notification technique, see U.S. Pat. No. 7,272,436 to Gill et al.

If a bedside monitor or other external monitor is provided, the bedside monitor provides audible or visual alarm signals to alert the patient or caregivers, as well as providing textual or graphic displays. In addition, PAP data and other diagnostic information is transferred to the bedside monitor or is stored within the CRMD device for subsequent transmission to an external programmer for review by a clinician or other medical professional. The clinician may then prescribe therapies to address various medical conditions. The clinician may also adjust the operation of the CRMD to activate, deactivate or otherwise control any therapies that are automatically applied. The bedside monitor may be networked with a centralized processing system 118 and/or a remote clinician review system 120 to immediately notify the clinician of any urgent medical condition such as a significant progression in MR due to HF. If life-threatening conditions are detected, emergency personnel are preferably notified immediately. Techniques for automatically notifying emergency personnel of serious medical conditions are discussed, for example, in U.S. Published Application No. 2011/0066055 of Bharmi et al.

Hence, FIGS. 1 and 2 provide an overview of exemplary medical systems for detecting MR based on PAP, optimizing pacing parameters, recording diagnostics and delivering appropriate warning/notification signals, etc. Note that the particular locations of the implanted components shown in FIGS. 1 and 2 are merely illustrative and may not necessarily correspond to actual implant locations.

PAP-Based Techniques for Detecting MR

Figure 3:
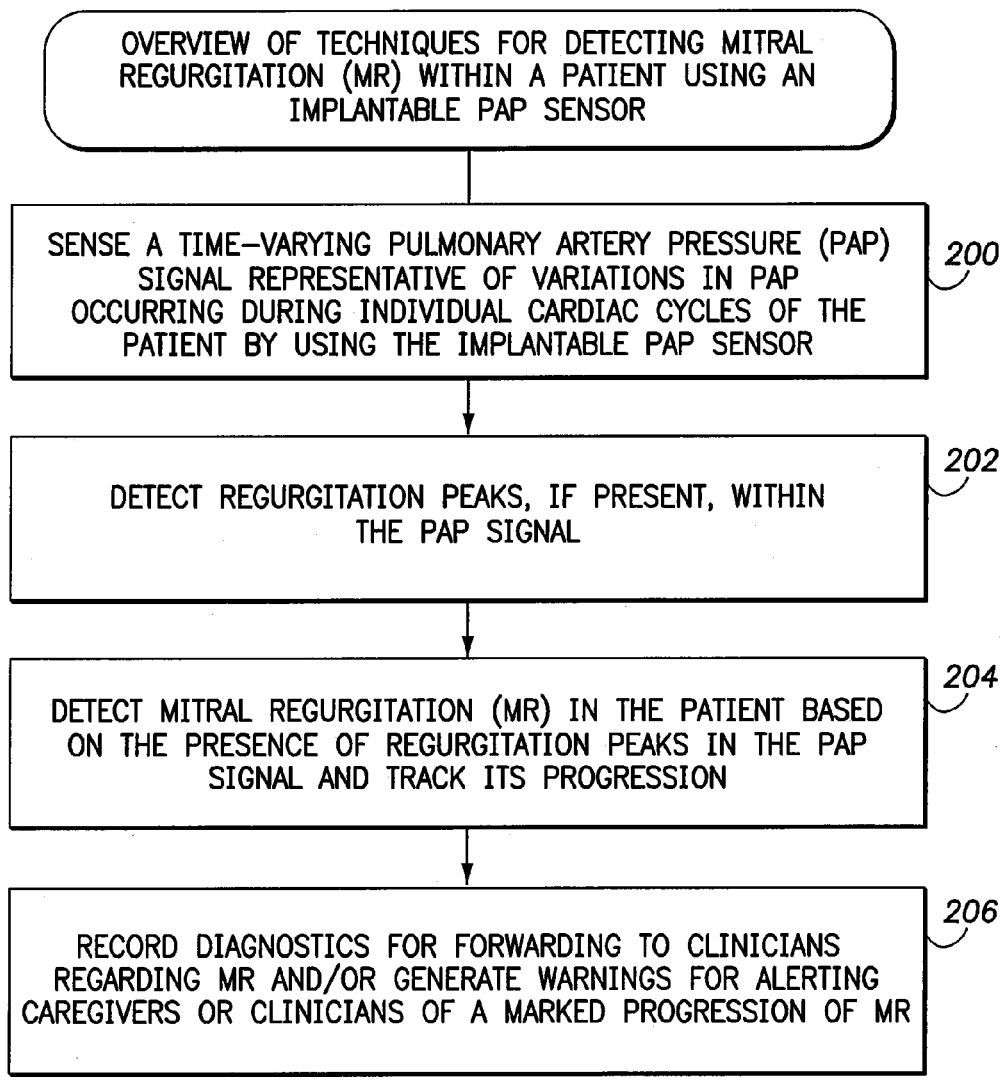
FIG. 3 summarizes a general technique that may be performed by the systems of FIG. 1 or 2 to detect MR based on PAP waveforms.
Figure 4:
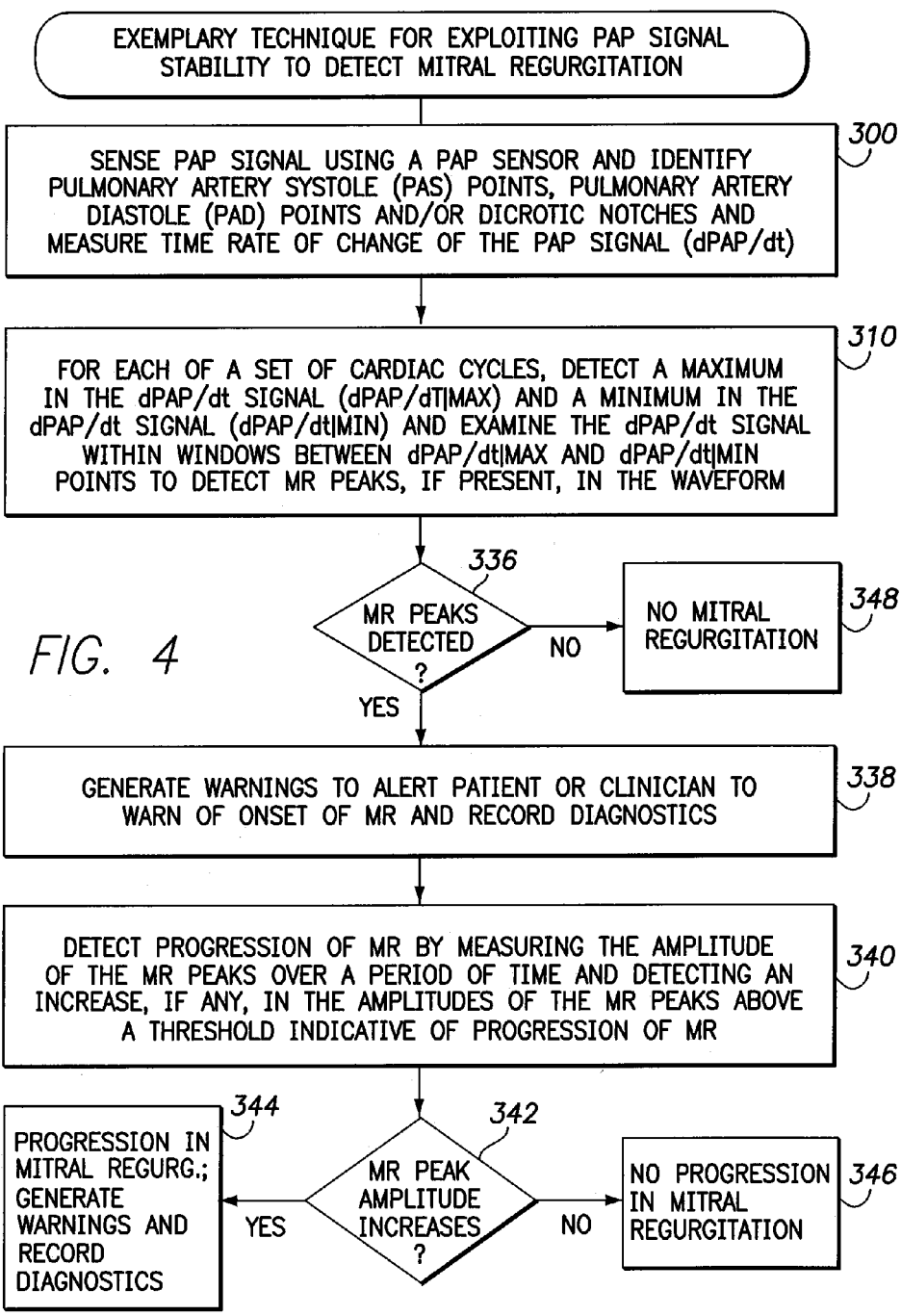
FIG. 4 illustrates an exemplary technique for use with the general method of FIG. 3, wherein a windowing process is used to isolate and detect regurgitant peaks within PAP waveforms for use in identifying and tracking MR.

FIG. 3 broadly summarizes the techniques exploited by the PAP monitoring systems of FIGS. 1 and 2 (or other suitably-equipped systems) for detecting and tracking MR. Briefly, at step 200, the system senses PAP signals using an implanted PAP sensor in communication with a PAP monitor (which, as noted, may be an external system or a component of a CRMD.) The sensed PAP waveform is primarily representative of pressure changes in the pulmonary artery and typically includes pulmonary artery systole (PAS) points, pulmonary artery diastole (PAD)/pulmonary artery end diastolic pressure (PAEDP) points, and dicrotic notches. At step 202, the system detects regurgitation peaks, if present, within the PAP signal, such as by using a windowing technique described below. At step 204, the system detects MR based on the presence of the regurgitation peaks within the PAP signal and tracks its progression over time such as by repeating the procedure once per day to detect changes in MR peak amplitudes. At step 206, the system records diagnostics for forwarding to the clinician regarding MR such as PAP waveforms. If PAP monitoring is performed once per day by an external system, the system can thereby provide daily trending of MR while pairing that information with hemodynamic data such as PAP morphology data, PAS peak amplitudes, PAD peak amplitudes, etc. The technique can be exploited in combination with techniques described in U.S. patent application Ser. No. 13/681,241, of Ngo et el., filed Nov. 19, 2012, entitled "Systems and Methods for Exploiting Pulmonary Artery Pressure Obtained from an Implantable Sensor to Detect Cardiac Rhythm Irregularities," which is fully incorporated by reference herein.

At step 206, the system can also generate warnings for immediately alerting caregivers or emergency personnel of a significant progression of MR (particularly if the PAP monitor is an on-board component of a CRMD and hence can analyze PAP signals throughout the day.)

Turning now to FIGS. 4-7, exemplary techniques for exploiting PAP waveforms to detect MR will be described in detail. At step 300 of FIG. 4, the PAP monitor senses the PAP signal using a PAP sensor and identifies PAS points, PAD points, dicrotic notches or other fiducial points and measures the time rate of change of the signal (dPAP/dt.) In one example, an eighteen second continuous PAP waveform is obtained and analyzed, though shorter or longer segments of data may alternatively be collected for analysis. For implementations where an external PAP monitor is used, the data is collected periodically, such as once per day, or is collected on demand if the patient feels symptomatic.

Figure 5:
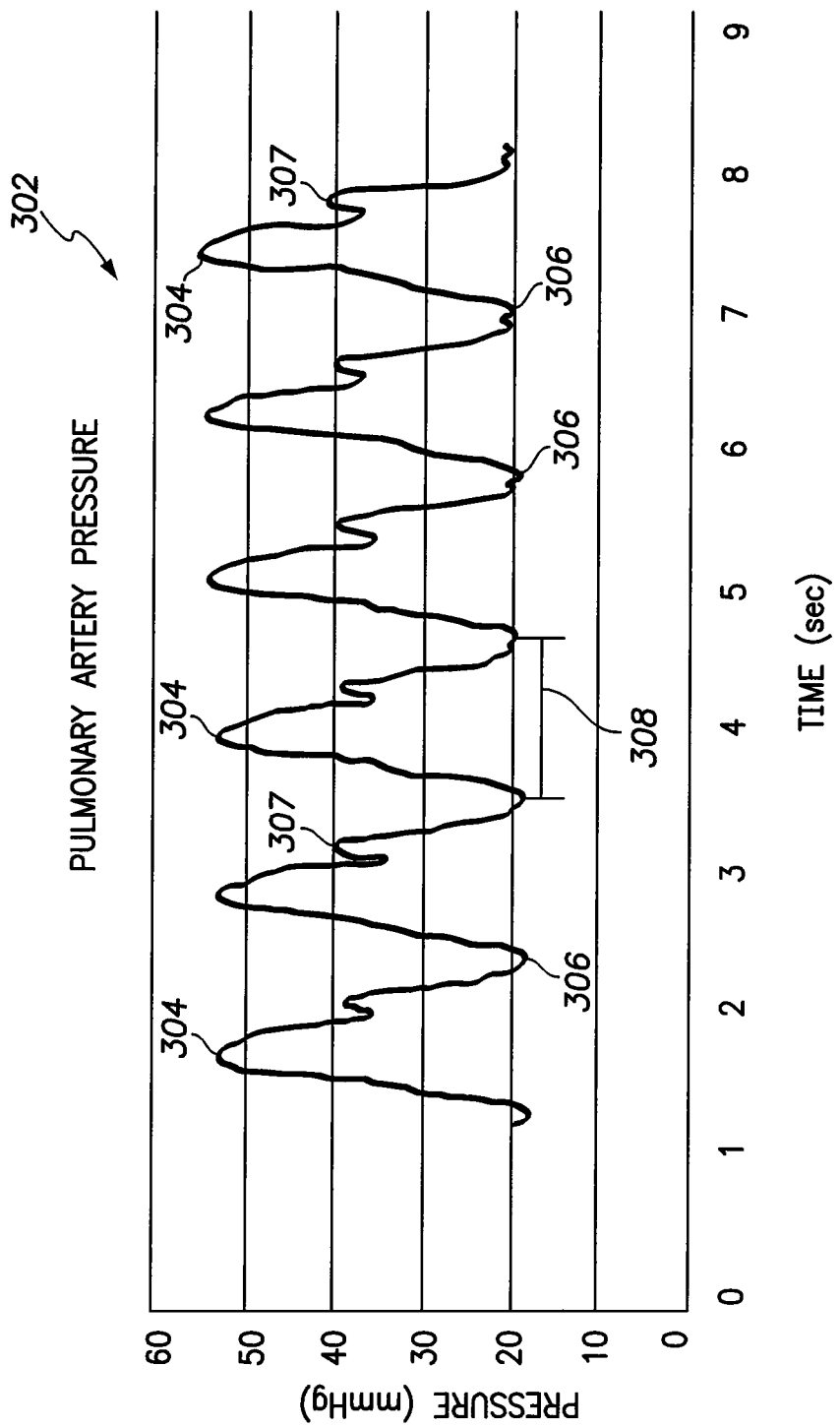
FIG. 5 graphically illustrates exemplary PAP waveforms that may be analyzed by the technique of FIG. 4, specifically highlighting fiducial points that may be detected and exploited.

FIG. 5 illustrates a time-varying PAP signal or waveform 302 showing PAS points 304, as well as PAD/PAEDP points 306 and dicrotic notches 307. An exemplary interval 308 is shown between a pair of the PAD points, which corresponds to the duration of a corresponding cardiac cycle. Note, however, that the start and end points of the PAP interval will not necessarily correspond to the start and end points of the corresponding electrical cardiac cycle as observed within an IEGM or surface EKG. For example, within the IEGM an intrinsic cardiac cycle is typically deemed to begin with the P-wave (corresponding to atrial depolarization.) This is followed by a QRS complex (or R-wave), which corresponds to ventricular depolarization. The QRS-complex is then followed by a T-wave (corresponding to ventricular repolarization.) Hence, within the IEGM, an intrinsic cardiac cycle is deemed to extend from P-wave to P-wave. If the atria are paced, the paced cardiac cycle is deemed to extend from A-pulse to A-pulse. Within the PAP waveform, PAS typically occurs after the QRS and before the end of the T-wave. This pressure is at the peak of the PAP waveform. PAD/PAEDP occurs at the end of the QRS complex where a sharp systolic upstroke begins. An ideal PAP waveform will have a smooth progressive diastolic runoff to end diastole and a smooth systolic upstroke. The PAEDP and the minimum PAD will thus be equal. The dicrotic notch occurs after the T-wave on the downstroke of the PA wave from pulmonic valve closure. If MR is present, an MR peak (not shown in FIG. 5) may appear in the PAP signal. Note that the MR peak is more readily detectable within the dPAP/dt signal, rather than in the PAP signal itself, and so the exemplary techniques herein exploit dPAP/dt.

Returning to FIG. 4, at step 310, for each of a set of cardiac cycles, the system detects a systolic maximum in the dPAP/dt signal (dPAP/dt|max) and a diastolic minimum in the dPAP/dt signal (dPAP/dt|min) corresponding to individual cardiac cycles and examines the dPAP/dt signal within windows between dPAP/dt|max and dPAP/dt|min to detect MR peaks, if present, in the waveform. Note that the dPAP/dt|max point is detected by examining the dPAP/dt signal after PAP begins to increase from a prior PAD point to a new PAS point to identify the highest amplitude point within the dPAP/dt signal prior to the PAS point of the new PAP waveform. Likewise, the dPAP/dt|min point is detected by examining the dPAP/dt signal after the PAP signal begins to decrease toward its PAD point to identify the lowest amplitude point within the dPAP/dt signal following PAS and prior to the dicrotic notch. This allows other local maxima or minima in the dPAP/dt signal (including any local max or min associated with the dicrotic notch) to be ignored for the purposes of defining the MR peak search window. Note that the dicrotic notch may be advantageously detected for other purposes as well, such as to measure and quantify morphology changes of the dicrotic notch over time for use in evaluating hemodynamic performance related to valve function, especially the pulmonic valve. (In this regard, although the PAP signal might not provide much information relating to the aortic valve, it could be used as an indicator of pulmonic valve function. In particular, any dramatic changes in amplitude or timing in reference to the PAS and PAD may indicate a change in valve function.)

Once the search window has been established, the system detects the MR peak by looking for positive upslopes in the PAP signal beyond a predetermined threshold. The threshold may be set as a change in the slew rate of the signal or by way of a moving average threshold. Inherently the differentiated signal will be noisier and so a moving average threshold allows for changes in dPAP/dt due to outliers or small variations to be ignored. Other methods to avoid falsely identifying the mitral regurgitant peaks include applying a low pass filter to the PAP signal prior to windowing.

Figure 6:
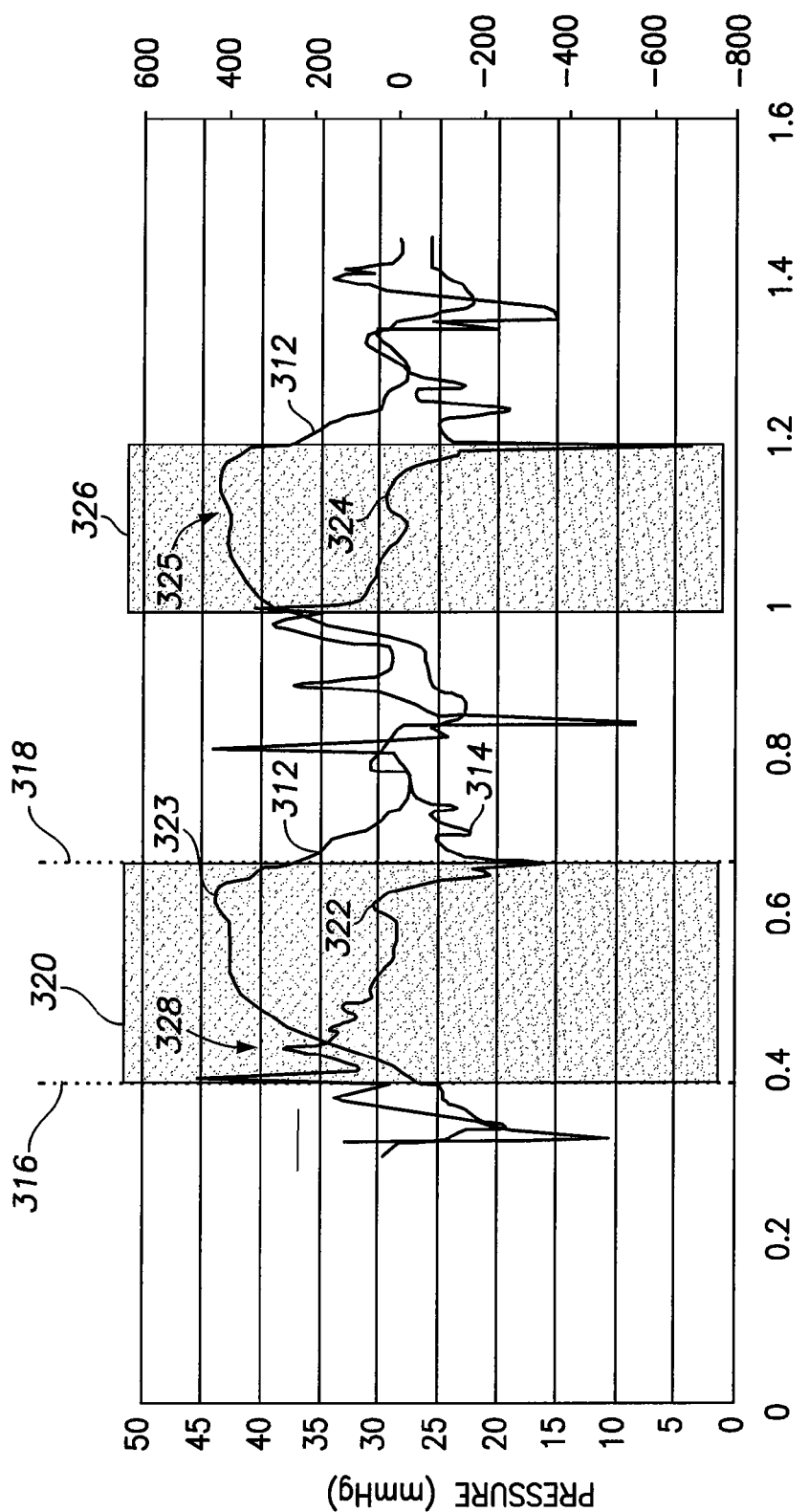
FIG. 6 graphically illustrates exemplary PAP waveforms that may be analyzed by the technique of FIG. 4, specifically highlighting windows used to isolate and detect regurgitant peaks within a patient with MR.

FIG. 6 shows an exemplary PAP signal 312 and dPAP/dt 314 for a couple of cardiac cycles for a patient with MR (with PAP in mmHg on the left vertical axis and dPAP/dt on the right vertical axis.) Within the PAP waveform of the first cardiac cycle, dPAP/dt|max occurs at time 316 and is followed by dPAP/dt|min point at time 318. These two points define a window 320 in which the PAP monitor searches for an MR peak 322 within the dPAP/dt signal that has a relatively large amplitude (sufficient to distinguish the MR peak from the sort of small variations in the dPAP/dt signal occurring even in the absence of MR) and is generally aligned with the PAS point 323 of the corresponding PAP signal. A second waveform shows another MR peak 324 within a window 326. As can be seen, the MR peaks are more pronounced within the dPAP/dt signal than in the corresponding PAP waveforms, making MR more readily detectable within the dPAP/dt signal. For example, contrast MR peak 324 of the dPAP/dt signal within window 326 with corresponding fluctuations 325 of the PAP signal.

The use of the detection window allows the system to search only within portions of the PAP waveform that would likely include an MR peak to thereby eliminate most other peaks or fluctuations within the dPAP/dt signal from consideration. Note that the MR peaks are local peaks within the dPAP/dt signal, not absolute peaks, and so the MR peak does not necessarily correspond to the maximum value of the dPAP/dt signal within the window. For example, as shown within window 320, one or more other local peaks may appear within the dPAP/dt signal (such as peak 328) that are not MR peaks. However, unlike MR peak 322, these other peaks are not generally aligned with the PAS peak of the PAP signal and hence can be rejected as not being a true MR peak. In this regard, one expects the MR regurgitation to be near the PAS. Additionally, the system may tighten or shorten the window to reduce the potential of picking up the noise. Another option is to smooth the PAP signal prior to differentiating the signal to clean up the dPAP/dt signal. Yet another option is to have a programmable function that allows the clinician to manually mark/adjust valve closure on the PAP waveform via external programmer during echocardiography or while using graphical display systems such as the Ensite™ of St. Jude Medical. A template acquisition algorithm/procedure can be used for future reference.

Figure 7:
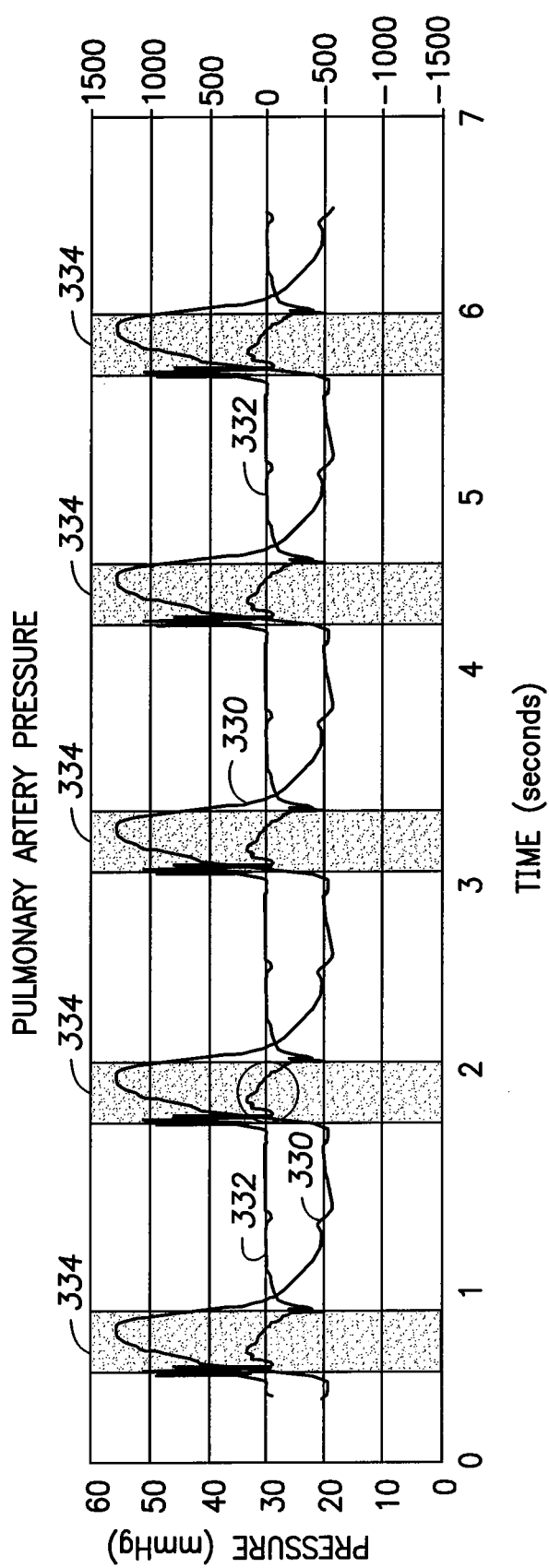
FIG. 7 graphically illustrates exemplary PAP waveforms that may be analyzed by the technique of FIG. 4 within a patient without MR.

FIG. 7 shows another exemplary PAP signal 330 and corresponding dPAP/dt signal 332 for a couple of cardiac cycles for a patient without MR. Also shown are various detection windows 334. As can be seen, the dPAP/dt signal of this example does not exhibit any sufficiently large local peaks within the detection windows indicative of MR peaks and hence the PAP waveform is not indicative of MR. Note that there are some relatively small fluctuations within the dPAP/dt signal within the window, but none sufficiently large to trigger detection of an MR peak. (In this regard, the system may be programmed to compare any fluctuations found within the dPAP/dt signal window to a minimum deviation threshold set to distinguish MR peaks from non-MR signal fluctuations. Such a threshold may be determined in advance based on analysis of dPAP/dt signals for PAP waveforms where it is know in advance whether the patient has MR.)

Returning to FIG. 4, when a mitral regurgitant peak has been identified in the dPAP/dt signal, a temporal correlation to the PAP signal may be performed to identify the corresponding PAP|regurg peak (i.e. MR peak) in the PAP signal for tracking to determine any worsening of regurgitation. A change in the MR peak may be calculated as a percent change from baseline (if baseline regurgitation measurement is available or inter-peak isoelectric line may be used) or absolute change. Exceeding a programmable threshold triggers an alert to be sent to the physician or noted on the data recording for review. That is, at step 336, if MR peaks are detected within each of the detection windows that are examined (or within a majority of such windows), MR is thereby indicated and, at step 338, the system generates warnings to alert the patient or clinician to warn of onset of MR and records diagnostics (such as the PAP waveforms, dPAP/dt signals, etc.) As can be appreciated, a relatively large number of PAP waveforms corresponding to a relatively large number of cardiac cycles are preferably examined by the system before an indication of MR is made so as to prevent a few false positive MR peak detections from triggering an MR warning.

At step 340, the PAP monitor then detects progression of MR by measuring the amplitude of the MR peaks over a period of time and detecting an increase, if any, in the amplitudes of the MR peaks above a threshold indicative of progression of MR. If the amplitudes of the MR peaks are found to increase significantly over time at step 342, progression of MR is thereby indicated at step 344. The system then generates additional warning signals to alert caregivers or other personnel. Otherwise, no progression in MR is indicated at step 346. Also, if MR peaks were not detected back at step 336, then no MR is indicated at step 348. Although not explicitly shown, following steps 344, 346 or 348 of FIG. 4, processing returns to step 300 so that the PAP monitor may sense and analyze additional PAP signals, periodically, continuously or on-demand.

Thus, the techniques of FIGS. 4-7 leverage a dynamic windowing procedure using dPAP/dt|max (systolic) and dPAP/dt|min (diastolic) points of the PAP waveform to monitor for the MR peak and measure its amplitude. This allows for the physician or clinician to observe the MR peaks and to be alerted to changes in mitral insufficiencies. In particular, the dynamic windowing of the dPAP/dt waveform allows for the pertinent time interval to be narrowed to assess mitral regurgitant waveforms. Without using of dPAP/dt, it would be difficult to separate the PAS peak from the regurgitant peak (i.e. the MR peak) within the PAP signal. If the PAP monitor is a component of a CRMD, the device may use additional or alternative techniques for detecting MR, such as techniques exploiting heart sounds or impedance vector measurements. If so, the CRMD may use the PAP-based analysis of FIGS. 4-7 to corroborate the MR determination while also providing additional PAP-based diagnostic data. Techniques for use by CRMDs for detecting MR based on heart sounds or other parameters are discussed, for example, in: U.S. Published Application No. 2012/0158079 of Rosenberg et al., U.S. Pat. No. 7,139,609 to Min et al., and U.S. Pat. No. 7,848,793 to Shelchuk et al. For implementations where the PAP monitor is an external system that receives PAP signals wirelessly from the implanted PAP sensor, the patient may be instructed to activate the system once per day so that the PAP monitor can collect PAP data for performing the MR analysis.

PAP-Based Techniques for Optimizing Pacing Delays

Figure 8:
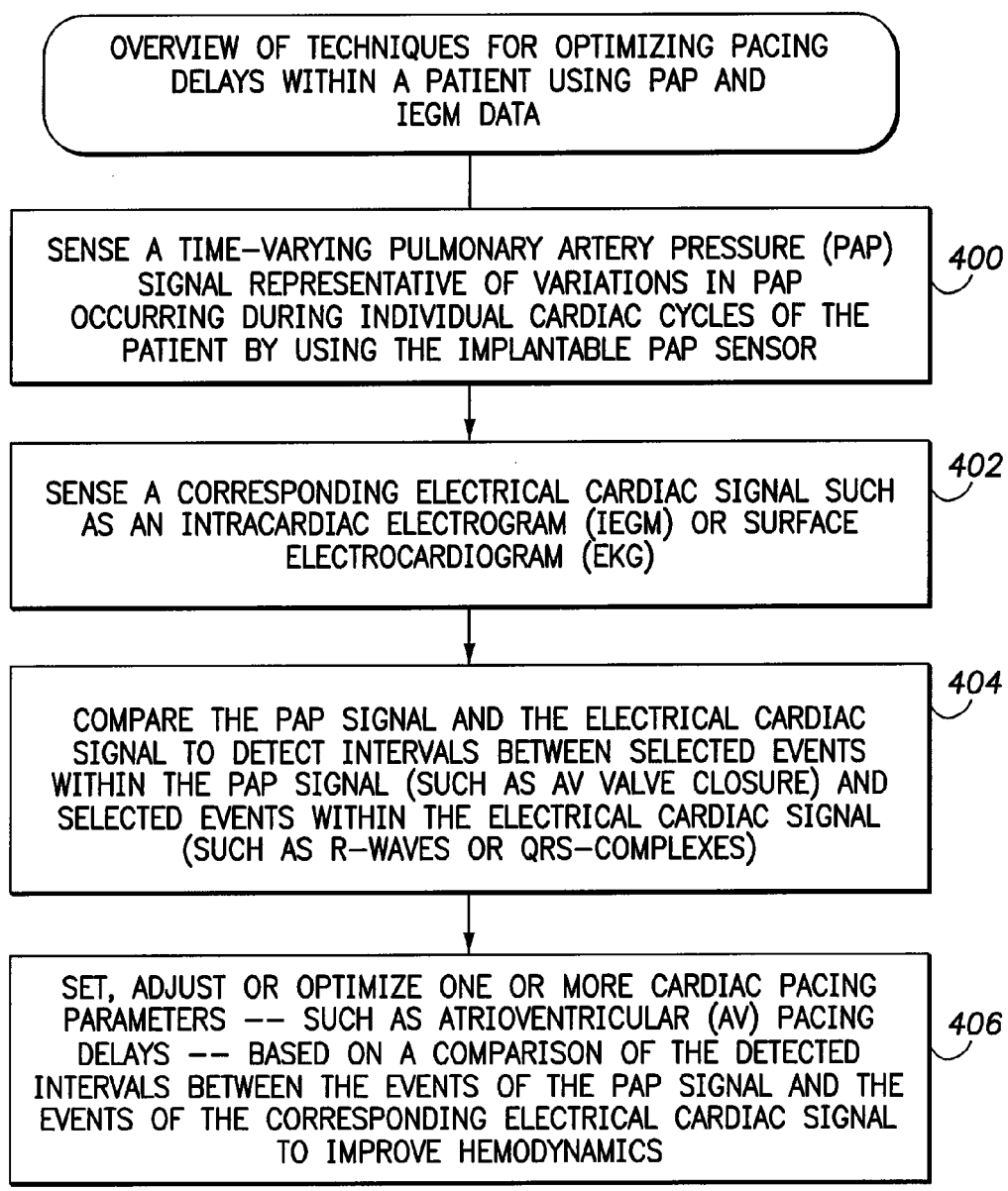
FIG. 8 summarizes a general technique that may be performed by the system of FIG. 2 to optimize pacing delays based on PAP signals and other signals detected by the CRMD.

FIG. 8 broadly summarizes techniques for use by the CRMD of FIG. 2 (or other suitably-equipped systems) for optimizing pacing parameters based, at least in part, on PAP signals. Alternatively, the optimization procedures may be exploited by external systems such as device programmers based on PAP data (and other data) received from a CRMD, such as may be performed during a follow-up session with a clinician following device implant. Note that some of the steps of FIG. 8 are the same or similar to those described above and hence will not be described again in detail. At step 400, the system senses time-varying PAP signals representative of variations in PAP occurring during individual cardiac cycles of the patient by using the implantable PAP sensor. At step 402, the system senses a corresponding electrical cardiac signal such as an IEGM or surface EKG. At step 404, the system compares the PAP signal and the electrical cardiac signal to detect intervals between selected events within the PAP signal (such as AV valve closure events) and selected events within the electrical cardiac signal (such as R-waves or QRS-complexes.) At step 406, the system sets, adjusts or optimizes one or more cardiac pacing parameters—such as AV delays—based on a comparison of the detected intervals between the events of the PAP signal and the events within the corresponding electrical cardiac signal to improve hemodynamics.

For example, the AV delay may be set based on the time interval between closure of the AV valves (detected using the PAP waveform) and the R-wave (detected within an IEGM) so that the atrial kick provided by contraction of the atria has completed before ventricular depolarization such that the ventricular chambers do not eject against an open AV valve. In this regard, the AV valves (i.e. the mitral valve and the tricuspid valve) close due to pressure gradients in the antegrade chamber creating back pressure to push the AV valve leaflets closed. AV pacing delay values are adjusted based on the detected time interval so that the appropriate atrial kick has completed before ventricular contraction. (Note that the mitral valve typically closes slightly before the tricuspid valve (~0.04 sec) but this slight difference may be disregarded for the purposes of setting the AV pacing delay.) As an option for stand-alone PAP devices, this type of AV optimization could also be done using the dicrotic notch and window timing only. If dicrotic notch moves too close to peak PAP, this generally signifies A-wave cut off (i.e. loss of filling.) If dicrotic notch falls late or outside a specified window, the AV delay is deemed to be too long.

If implemented within a CRMD, the optimization procedure of FIG. 8 may be performed once per week (or at some other predetermined interval) to provide periodic optimization of pacing parameters to maintain the parameters at or near optimal values to improve hemodynamics. In other examples, the CRMD might perform the optimization in response to some triggering event, such detection of the onset of MR. In other implementations, the optimization will be performed only under clinician supervision using an external programmer. It should be understood that "optimal" pacing parameters obtained using techniques described herein are not necessarily absolutely optimal in a given quantifiable or mathematical sense. What constitutes "optimal" depends on the criteria used for judging the resulting performance, which can be affected by many factors and can be subjective in the minds of some clinicians. The pacing parameters set using techniques described herein represent, at least, "preferred" pacing parameters. Clinicians may then choose to adjust or alter these parameters at their discretion using an external device programmer. Note also that the optimization technique of FIG. 8 can be exploited in combination with the MR detection techniques described herein, and further in combination with the techniques described in the Patent Application of Ngo et al. incorporated by reference above.

Hence, timing optimization can be accomplished using cardiac hemodynamic indicators of the PAP waveform. In instances in which MR is present, the interventricular mechanical delay can be observed hemodynamically based on the interval between the double peaks in the PAP waveform (where the first peak is the PAS peak and the second peak is the MR peak.) This inter-peak interval corresponds to the interventricular mechanical delay because the PAS peak is associated with the maximum pressures generated by contraction of the RV; whereas the MR peak is associated with the maximum pressures generated by contraction of the LV (which causes MR jets via regurgitation back into the LA.) Hence, the interval between PAS peak and MR peak provides a proxy for interventricular mechanical delay within patients with MR.

Leveraging the double peaks during timing optimization of interventricular delay as well as optimal electrode placement acutely and chronically to minimize the delay between these peaks may be used. In practice, the same windowing as described above can be used to identify the second peak to calculate an inter-peak delay and may be annotated to the physician while selecting the best VV timing or electrode placement/configuration. In addition, AV delay optimization can be accomplished by monitoring and marking the dicrotic notch and the closure of the AV valves. As noted, the dicrotic notch represents the closure of the pulmonic and aortic valves (triggering the S2 heart sound.) The subsequent closure of the AV valves occurs by way of the pressure gradient in the antegrade chamber creating back pressure to push the valve leaflets closed (triggering the S1 heart sound.) The goal of AV optimization is to ensure that the appropriate atrial kick has completed and the ventricular chamber does not eject against an open AV valve. Using the PAP waveform, the system (or a clinician operating the system) may leverage the surface ECG or IEGM to guide AV optimization ensuring the appropriate hemodynamic state. This can be accomplished by allowing the AV valve closure to occur before ventricular activation and/or by using a programmable delay between AV valve closure and ventricular activation.

Turning now to FIGS. 9A-12, exemplary techniques for exploiting PAP waveforms to optimize pacing parameters will be described in detail. In this example, the optimization is performed by a CRMD but, as noted, external systems may additionally or alternatively be used to perform the optimization. At step 500 of FIG. 9A, the system: senses a PAP signal using an implantable PAP sensor; identifies PAS points, PAD points and dicrotic notches in the PAP waveform; and detects the closure of the AV valves using the PAP waveform (or using other signals such as heart sound signals, if available.) As noted, the AV valves close as intraventricular pressure exceeds atrial pressure. Closure of the AV valves triggers the first heart sound (S1) and is followed by a rise in blood pressure in the LV and RV as the ventricles contract isovolumetrically. The sharp rise in ventricular pressure soon causes the aortic and pulmonic valves to open, in turn triggering a sharp increase in aortic pressure as blood flows from the LV into the aorta and a sharp rise in PAP as blood flows from the RV into the pulmonary artery. Eventually, pressures within the ventricles drops below pressures in the aortic and pulmonary arteries and so the aortic and pulmonic valves close again (triggering the S2 heart sound and causing the dicrotic notch in the PAP signal and a corresponding notch in an aortic pressure waveform.) The ventricles relax isovolumetrically until the AV valves reopen once pressure in the atria again exceeds pressure in the ventricles. Accordingly, the closure of the AV valves can be detected for the purposes of ensuring the AV valves close before ventricular contraction. Using the PAP signal, the system at step 500 detects a point where the PAP pressure waveform reaches or approaches its lowest value (i.e. PAD.) That is, the onset of the PAP waveform may be interpreted as the closure of the AV valves.

At step 502, the system senses corresponding IEGM or ECG signals and detects R-waves (i.e. QRS-complexes) representative of ventricular depolarization. Note that the ventricular depolarization observed within the ECG is typically referred to as a QRS-complex whereas the same event within the IEGM is often referred to as the R-wave or "VS/VP". At step 504, for each cardiac cycle, the system verifies that AV valve closure occurs before the R-wave and measures the relatively short interval (DeltaTime1) between AV valve closure and the peak of the R-wave for comparison against an acceptable threshold or range of values. If at step 506, the AV valves do not close before the R-wave or if the DeltaTime1 value is not sufficient for proper hemodynamics, the system adjusts the AV delay while holding the VV pacing delay constant at step 507 and repeats the process. Adjustments to the AV delay may be made incrementally within a predetermined range of values until a hemodynamically appropriate interval is established between AV closure and R-wave (as maybe be specified by a clinician.) To determine whether the delay interval (DeltaTime1) is sufficient, the system may specify a predetermined range of values (Range1) for use as a threshold. In one particular example, DeltaTime1 must exceed the range to be deemed to be hemodynamically acceptable. Note that if the system is unable to identify an AV pacing delay sufficient to meet the criteria of step 506, warnings may be generated to notify the clinician that a problem arose with AV optimization and suitable diagnostics are recorded such as the AV pacing delay values that were tested and the resulting IEGMs and PAP signals Assuming that the AV pacing delay has been properly set, the system then proceeds to optimize the VV pacing delays. At step 508, for each cardiac cycle, the system detects MR peaks within the PAP signal and measures an interval (DeltaTime2) from PAS peak to MR peak (which is representative of the inter-ventricular delay) for comparison against another acceptable threshold or range of values. Note that if MR peaks are not present in the PAP signal because the patient does not have MR or because such peaks cannot be detected due to noise or other issues, then optimization of VV based on the PAP signal is not performed. Alternative VV optimization techniques may be used instead. Patents describing alternative techniques for optimizing AV and VV pacing delays are cited below.

Figure 10:
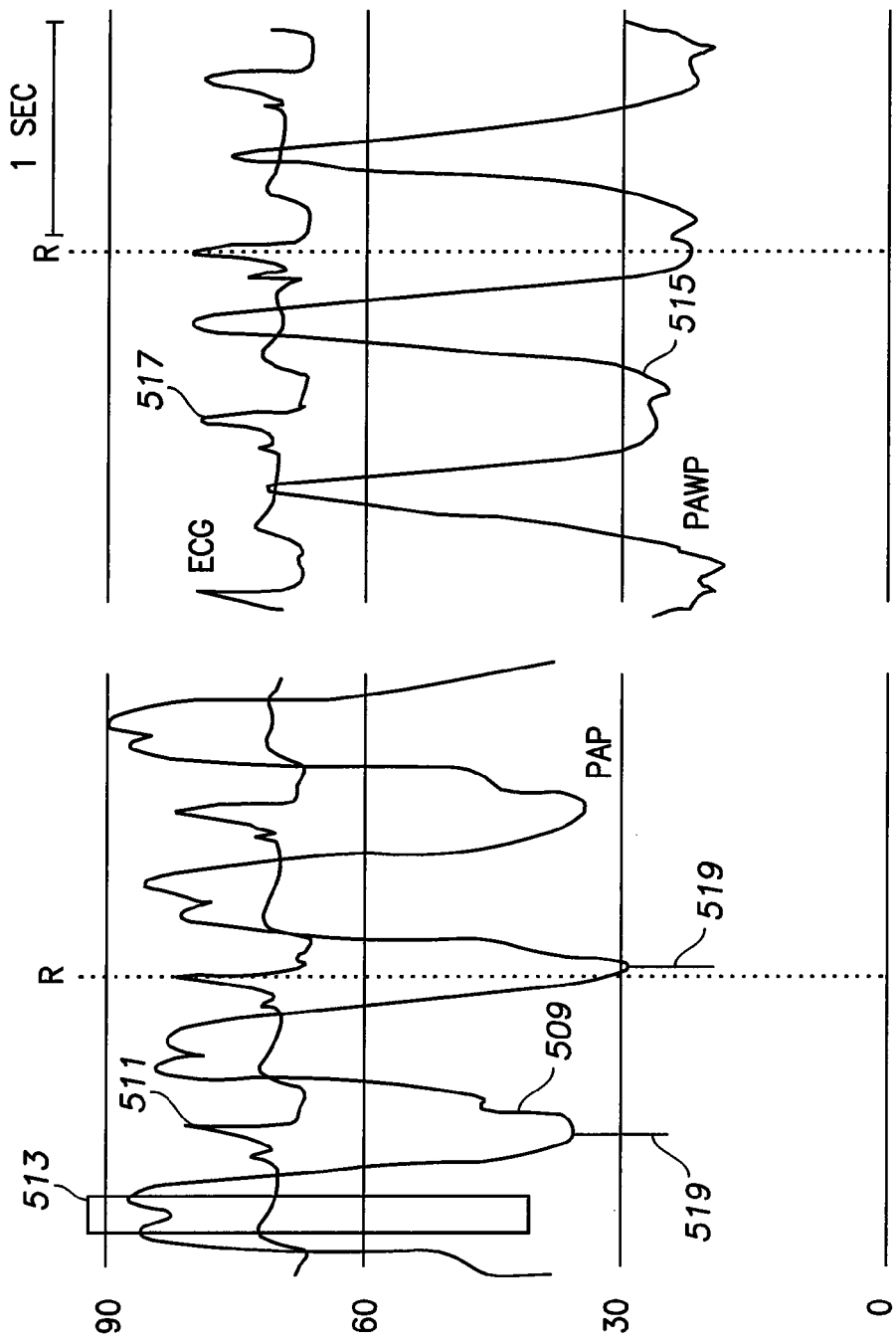
FIG. 10 graphically illustrates an exemplary pulmonary artery wedge pressure (PAWP) waveform and a surface EKG for a patient with MR showing an inter-peak delay pertinent to pacing optimization.
Figure 11:
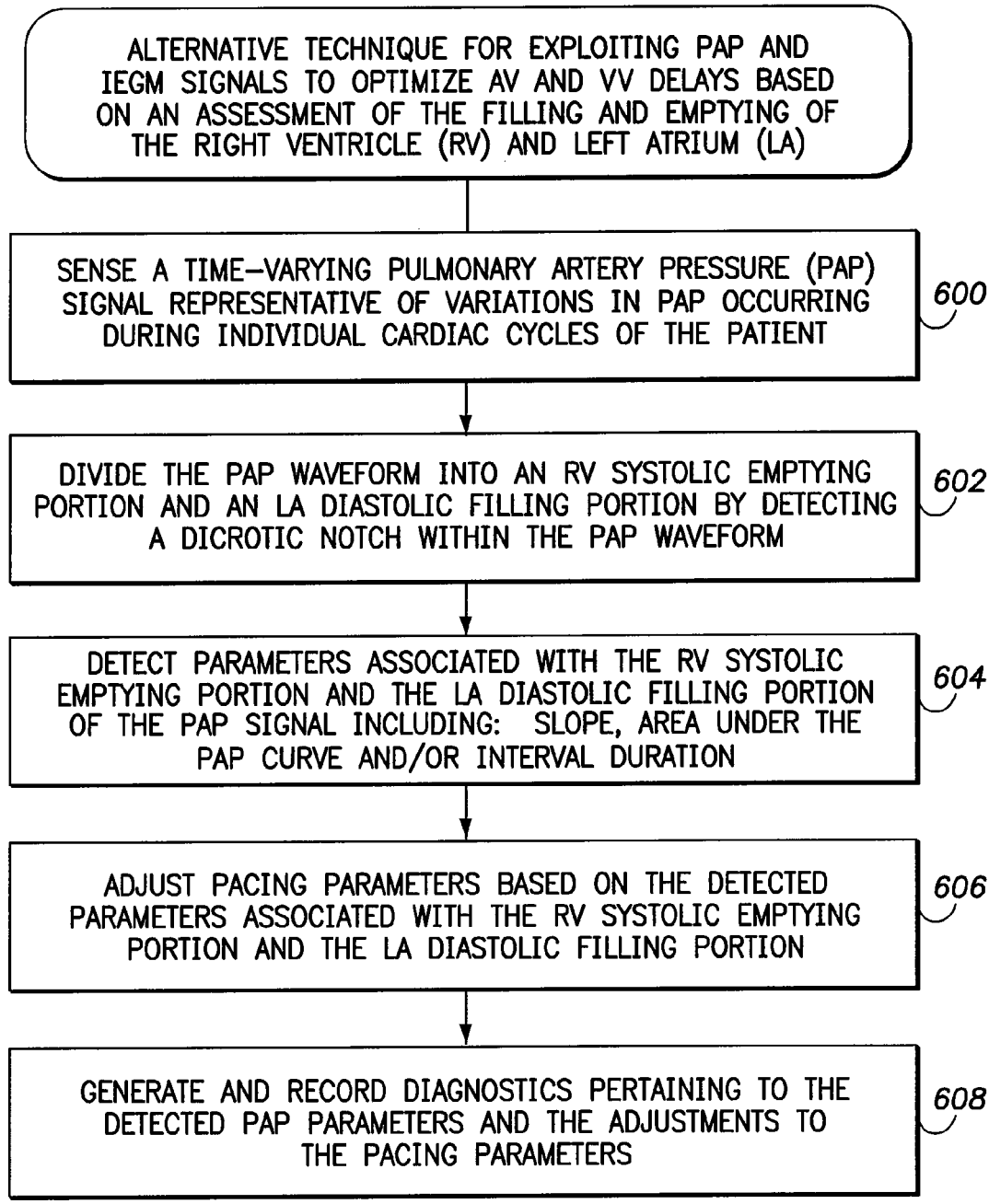
FIG. 11 illustrates alternative techniques that may be performed by the system of FIG. 2 for optimizing pacing parameters based on an assessment of portions of the PAP waveform associated with the filling and emptying of the RV and the LA.

FIG. 10 illustrates an exemplary PAP signal 509 and corresponding IEGM (or EKG) 511 for a patient with MR showing the inter-peak interval 513 between PAS peak and MR peak, which representative of the interventricular mechanical delay. For comparison, the figure also provides a corresponding PA wedge pressure (PAWP) trace 515 (as may be obtained by temporarily wedging a pulmonary catheter with an inflated balloon into a small pulmonary arterial branch to obtain pressure signals) and a surface EKG/ECG 517. (Note that the pressure traces and cardiac signal traces in the figure are redrawn from Mark JB: "Atlas of Cardiovascular Monitoring" New York, Churchill Livingstone, 1998: FIG. 17-11.) The interventricular mechanical delay is readily apparent within the PAP signal but not within the PAWP trace, thus illustrating one of the advantages of exploiting a PAP signal. The figure also identified points 519 within the PAP signal corresponding to the closure of the AV valves and onset of a new PAP waveform (which, in this example, occurs at about the same time as the peak of the R-wave.)

Returning to FIG. 9A, assuming that MR peaks are detected so that the interventricular mechanical delay (DeltaTime2) can be measured, then at step 512 the system determines whether DeltaTime2 is acceptable. If DeltaTime2 is not acceptable for proper hemodynamics, the system adjusts the VV pacing delay while holding the AV delay constant at step 514 and repeats the process. (Typically, the smaller the interventricular mechanical delay the better.) Adjustments to the VV pacing delay may be made incrementally within a predetermined range of values until the delay between the PAS peak and MR peak (i.e. DeltaTime2) is deemed to be hemodynamically acceptable or optimal. As with AV optimization, the system may specify a predetermined range of pacing delay values (Range2) for use as a threshold. If the system is unable to identify a VV pacing delay sufficient to meet the criteria of step 512, warnings are generated to notify the clinician that a problem arose with VV optimization and suitable diagnostics are recorded such as the current AV pacing delay, the VV pacing delay values that were tested and the resulting IEGMs and PAP signals. Thus, in addition to monitoring the progression of MR, the MR peaks are exploited to hemodynamically optimize VV delays to during implant and follow-up in reference to IEGM and/or surface EKG information.

Additional hemodynamic optimization procedures may be performed to improve CO and stroke volume. In this regard, at step 516, the system initiates hemodynamic optimization procedures while PVR is substantially constant within the patient. At step 518 of FIG. 9B, the system estimates a value that is proportional to CO while pacing is delivered using current AV and VV pacing delays by calculating (max PAP|mean−PAD) where CO=(max PAP−PAD)/PVR. In this regard, the following formulas apply (where PVP refers to pulmonary venous pressure):

$$\text{max PAP}=(\text{CO}\times\text{PVR})+\text{PVP} \quad (1)$$

$$\text{PVP}\sim\text{LAP}\sim\text{PAD} \quad (2)$$

$$(\text{max PAP}-\text{PAD})/\text{PVR}=\text{CO}, \quad (3)$$

where PVR is a constant and so CO is proportional to the pulmonary pressure gradient.

$$\text{SV}=\text{CO}/\text{HR} \quad (4)$$

Hence, so long as PVR remains substantially constant (such as if the patient is lying down while data is collected over a relatively short period of time), then the mean value of max PAP (where max PAP is the maximum value of the PAP signal during a cardiac cycle) minus the current PAD value is proportional to the current CO and hence PAP signals can be used to estimate CO and SV for timing optimization, lead placement and/or vector optimization both in an acute implant or chronic follow-up setting. That is, provided that the PAP measurements are done within one setting, the system can assume a substantially constant PVR thereby allowing for correlation of CO to PAP-PAD (or the pulmonary pressure gradient.)

At step 520, the system then adjusts AV, VV and/or LV inter-electrode pacing delays for CRT (and/or guides lead placement or the choice of pacing vectors) in an effort to increase max PAP|mean−PAD to thereby increase CO and SV, then compares max PAP|mean−PAD to a predetermined threshold representative of an acceptable or optimal value for CO. If at step 522, the value for max PAP|mean−PAD remains below the threshold, further adjustments are made to the pacing parameters and the process is repeated. Assuming, that an acceptable level of CO and SV has been achieved, the system then proceeds to step 524 to deliver CRT or other forms of pacing with the latest pacing delays while using the chosen pacing vectors.

Figure 9A:
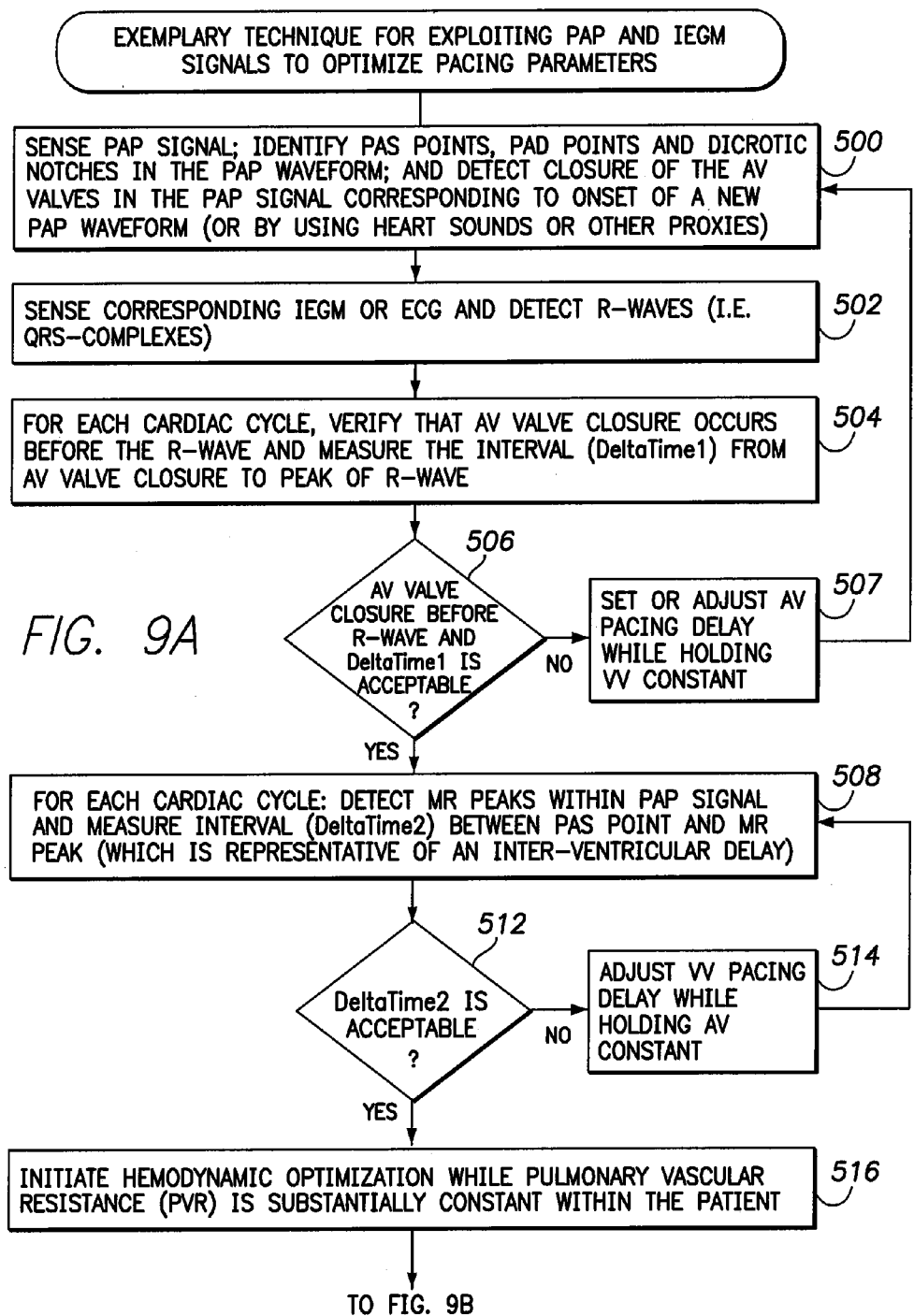
FIG. 9A and FIG. 9B illustrate an exemplary technique for use with the method of FIG. 8 for optimizing pacing parameters based on various time delay intervals detected within the PAP signal and a corresponding IEGM or surface EKG.
Figure 9B:
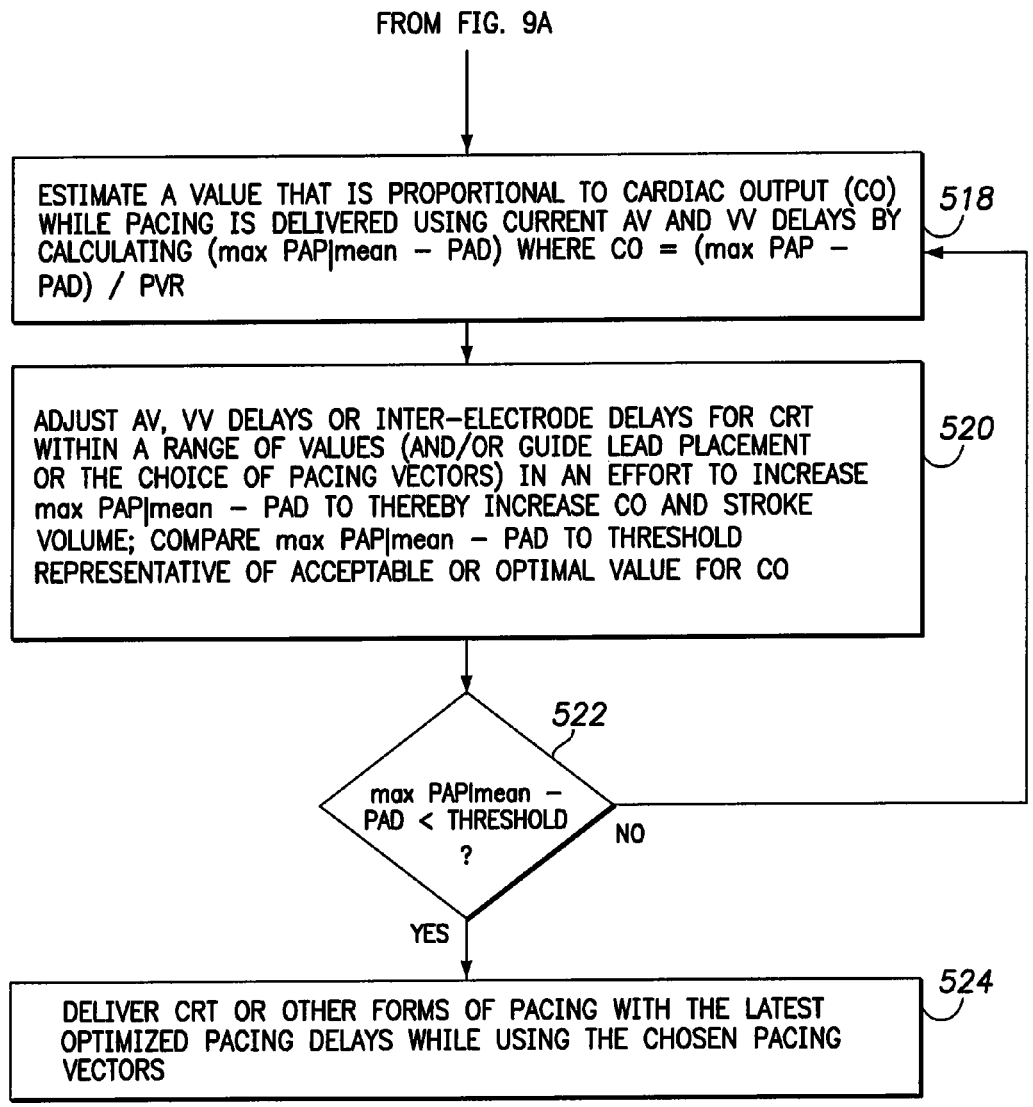

Note that the particular parameters to be adjusted using the technique of FIGS. 9A and 9B will depend upon the system and the circumstances in which it is implemented. If the method is performed by a clinician using an external system prior to final implant of pacing leads, the clinician may choose locations for lead placement (particularly the precise placement of an LV/CS lead for CRT) based on the optimization procedure. For example, CO may be evaluated based on PAP signals received while the LV/CS lead is positioned at various test locations so that the clinician can identify the particular location that provides the best CO. If the method is instead performed by a CRMD that has already been implanted within the patient, then lead location would not be adjustable but pacing delay values (AV, VV etc.) would be adjustable, as well as the particular pacing vectors to be used (especially if a multi-pole lead has been implanted for use with CRT.) Hence, a wide variety of optimization options may be exploited based on the needs of the clinician and the capabilities of system being used.

Figure 12:
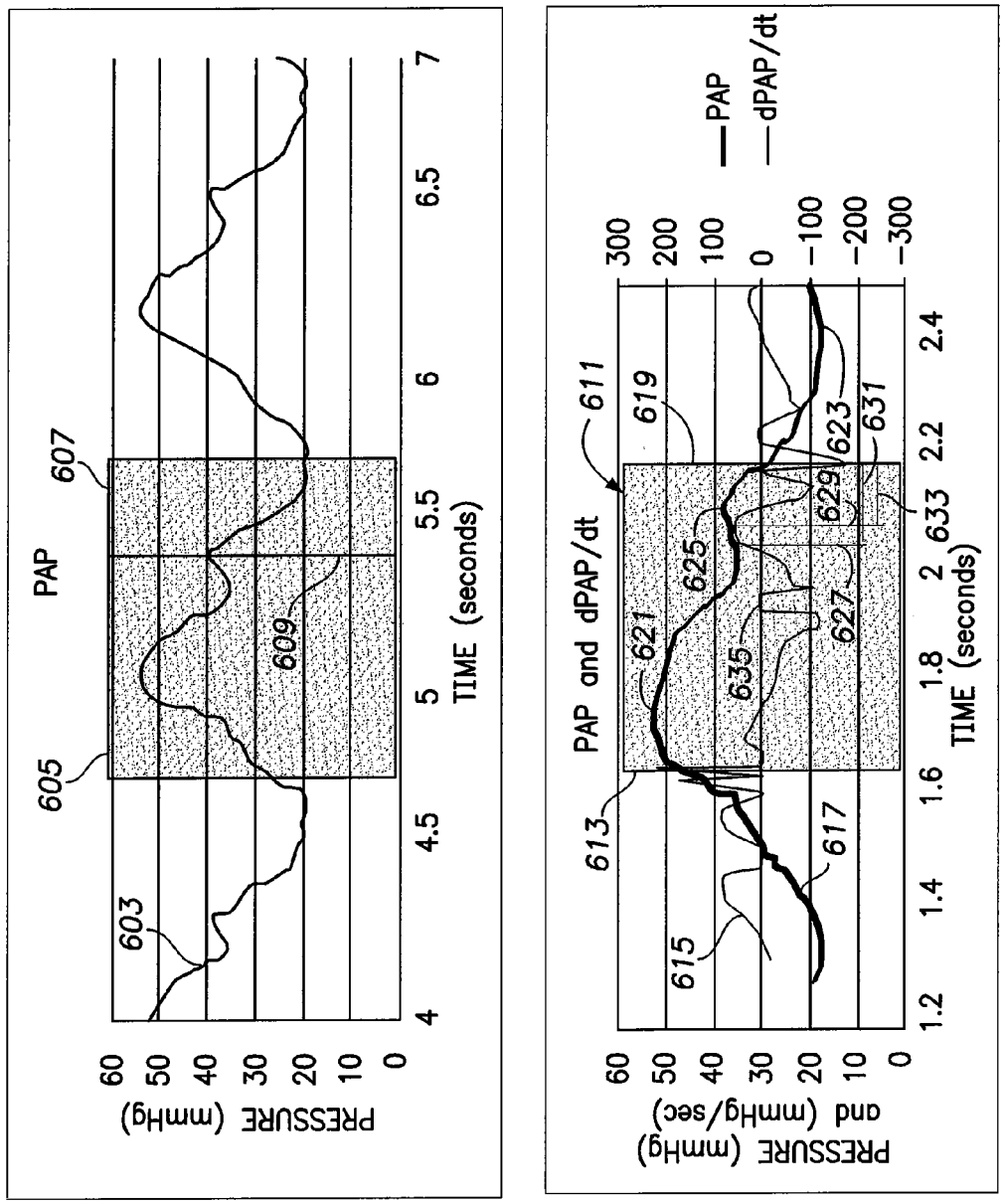
FIG. 12 graphically illustrates exemplary PAP waveforms that may be analyzed by the technique of FIG. 11, specifically highlighting portions representative of the filling and emptying of the RV and the LA.

FIGS. 11 and 12 illustrate additional or alternative optimization procedures based, at least in part, by segregated the PAP waveform into a RV systolic emptying portion and the diastolic filling of the LA by the dicrotic notch. The generally timing of the dicrotic notch can be determined by way of the dynamic windowing using dPAP/dt|max and dPAP/dt|min values similar to techniques described above. In addition, differentiating between the MR peak and the dicrotic notch may be achieved by measuring an inter-peak delay in which the time from the dPAP/dt|max and dPAP/dt|min to the middle peak is to measured and then, based on the relative closeness to the systolic RV peak or the diastolic minimum, the peak will be binned into an MR or a dicrotic notch bin. This inter-peak delay may also be programmable. After separating the emptying and filling portions of the PAP, the slopes of the independent portions of the PAP waveform may be optimized to increase filling and emptying efficiencies. In addition, other pacing parameters may be optimized in conjunction to the slopes including area under the curve and relative interval duration. These parameters may be used in for CRT optimization during implant or in a follow-up setting.

To this end, beginning at step 600 of FIG. 11, the system senses a time-varying PAP signal representative of variations in PAP occurring during individual cardiac cycles of the patient and then, at step 602, the system divides each detected PAP waveform into an RV systolic emptying portion and an LA diastolic filling portion by detecting a dicrotic notch within the PAP waveform. The first graph of FIG. 12 shows an exemplary PAP signal 603 with RV systolic emptying portion 605 and LA diastolic filling portion 607 separated by a dicrotic notch 609. The second graph shows the use of a detection window 611 similar to the one described above in connection with FIG. 6 but extending by an amount sufficient to include the dicrotic notch. As with the preceding example, the detection window begins with the dPAP/dt|max point 613 (between the prior PAD point and a new PAS peak) as detected within a dPAP/dt signal 615 derived from a PAP signal 617. In this case however, the window extends to the lowest dPAP/dt value 619 between the PAS peak 621 and the next PAD point 623 and hence covers the dicrotic notch 625.

Since this window will include the dicrotic notch as well as the MR peak, the system takes steps to the MR peak from dicrotic notch within the dPAP/dt signal. In one example, differentiating the MR peak from the dicrotic notch is achieved by first identifying closely adjacent local peaks 627 and 629 within the window between PAS peak 621 and dPAP/dt|min 619, then measuring intervals from those local peaks to dPAP/dt|min point (wherein the intervals are denoted 631 and 633, respectively, in the figure.) In this particular example, the peaks in dPAP/dt corresponding to the MR peak from the dicrotic notch are partially merged and, as such, it may be difficult for the device to automatically distinguish the peaks. In other examples, the MR peak would be more distinct. In practice, the intervals between the MR peak from the dicrotic notch are only measured if those peaks can be reliably detected and distinguished; otherwise the next PAP waveform is instead examined. (Note that peak 635 does not correspond to the MR peak and can be distinguished from a true MR peak based on its distance from the 613 dPAP/dt|max peak.) The intervals are examined to assess the relative closeness of the peaks to the dPAP/dt|min point (or some other fiducial point) to distinguish MR peak from dicrotic notch. In particular, as the dicrotic notch is expected to occur after the MR peak, the first of the two local peaks is binned as the MR peak and the second is binned as the dicrotic notch. Other discrimination techniques could instead be employed. In any case, once the dicrotic notch has been detected, the PAP signal can be then easily subdivided between RV systolic emptying portion and an LA diastolic filling portion so that these separate portions can be analyzed. Note also that some HF patients have diastolic MR due to too long a programmed AV delay allowing MR during diastole. This is can be addressed via AV optimization.

Returning to FIG. 11, at step 604, the system detects parameters associated with the RV systolic emptying portion and the LA diastolic filling portion of the PAP signal including: slope, area under the PAP curve and/or the relative interval durations of the two portions. At step 606, the system then adjusts pacing parameters based on the detected parameters associated with the RV systolic emptying portion and the LA diastolic filling portion to increase filling and emptying efficiencies. In particular, parameters such as the AV, VV or interelectrode pacing LV delays, the choice of pacing vectors, etc., are selectively adjusted based on the detected parameters. In general, pacing parameters are preferably adjusted to increase the slopes and the areas under the curves to thereby improve CO. Insofar as interval durations, pacing parameters may be adjusted to achieved some predetermined ratio of interval duration, such as two thirds RV emptying and one third LA filling (or as a percentage of the cardiac cycle where systole=⅓ of the cardiac cycle and diastole (filling) is ⅔ of the cardiac cycle.) The conditions to be achieved via optimization are preferably programmable and adjustable by the clinician to allow the clinician to control the optimization procedure. At step 608, the system generates and records diagnostics pertaining to the detected PAP parameters and the adjustments made to the pacing parameters for clinician review. As with the preceding examples, the particular parameters to be adjusted using the technique of FIG. 11 will depend upon the system being used and the circumstances in which it is implemented.

What have been described thus far are PAP-based techniques for detecting MR and optimizing pacing parameters. If the system is equipped to measure LAP (either directly or using a proxy for LAP), the aforementioned PAP-based techniques can be extended or modified to exploit LAP. Generally speaking, the above-described methods are modified to use the atrial and ventricular components of the LAP waveform, or additional LAP-based techniques are provided for which the PAP signal may not be well suited. Moreover, for timing optimization the ability to monitor both the atrial and ventricular portions of an LAP waveform allows for optimization of the area under the atrial portion of the curve to ensure that atrial kick is not truncated by a premature ventricular contraction (PVC.) Exemplary LAP-based techniques are described in the next section.

LAP-Based Techniques for Optimizing Pacing Delays

Figure 13:
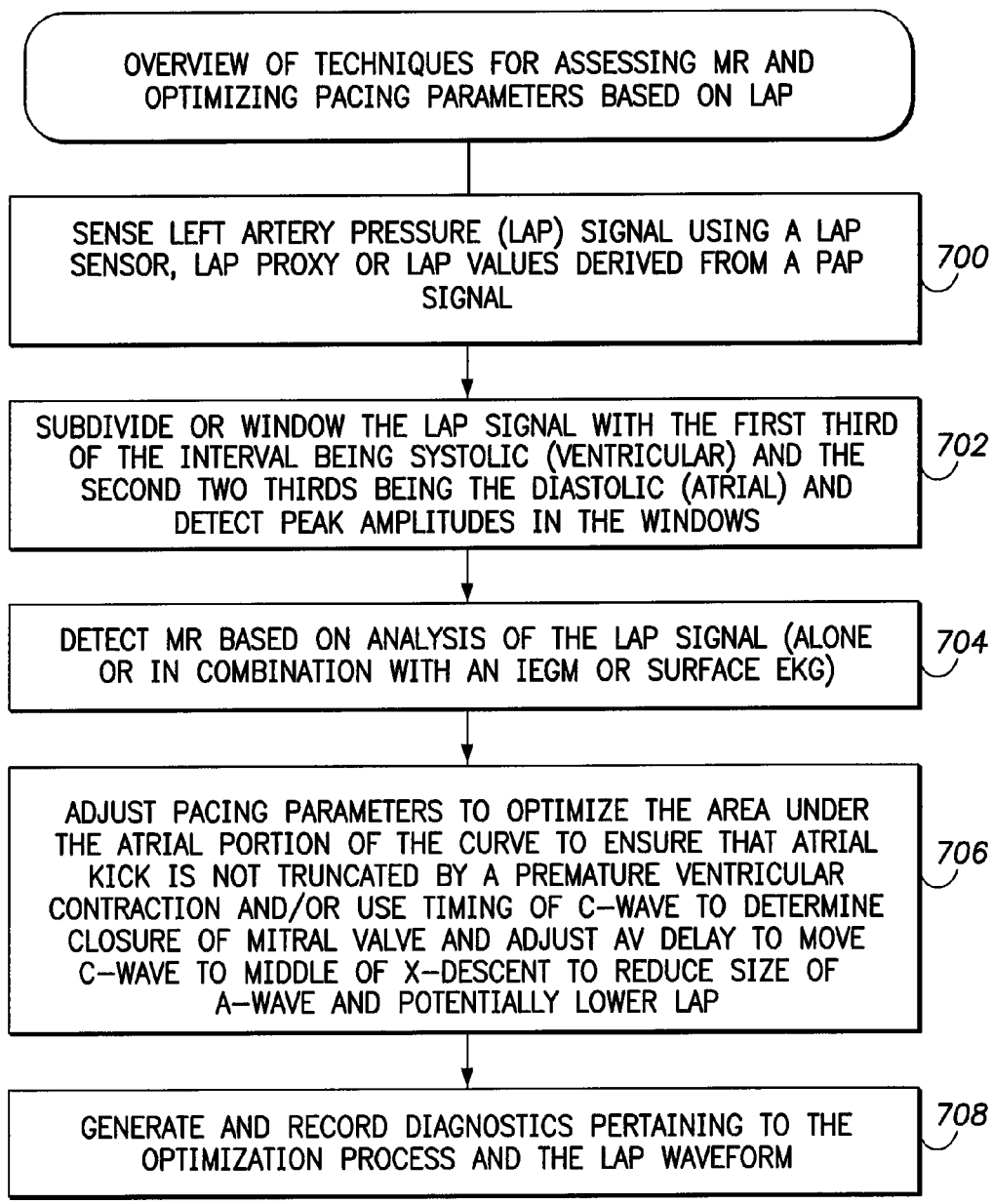
FIG. 13 illustrates alternative techniques for use with the methods of FIGS. 3-12 wherein LAP signals are additionally or alternatively exploited.

FIG. 13 broadly summarizes techniques for use by a CRMD (or other suitably-equipped systems) for optimizing pacing delays based, at least in part, on LAP signals. Alternatively, the optimization procedures may be exploited by external systems such as device programmers based on LAP data (and other data) received from a CRMD, such as may be performed during a follow-up session with a clinician following device implant. Beginning at step 700, the system senses time-varying LAP signals using an implanted LAP sensor, obtains LAP values using a suitable proxy, or derives LAP from the PAP signal. In particular, with the PAP sensor implanted as shown in FIG. 1, LAP data can be derived from the PAP signal since PAP is correlated to LAP, with the main difference being the gradient across the lungs and pulmonary veins. As such, the range of the PAP waveform does not drop to the typical diastolic pressures of the RV but maintains a slightly higher diastolic pressure level such as seen in the left atrium. Hence, in at least some embodiments, data obtained from the PAP sensor serves as a source for LAP values, particularly if no other source of LAP data is available such as an LAP sensor.

LAP sensors are discussed in, for example, U.S. Published Patent Application 2003/0055345 of Eigler et al., entitled "Permanently Implantable System and Method for Detecting, Diagnosing and Treating Congestive Heart Failure." Other techniques for detecting LAP that do not necessarily require an LAP sensor (such as by using cardiogenic impedance as a proxy) are discussed in U.S. Provisional Patent Application No. 60/787,884 of Wong et al., entitled, "Tissue Characterization Using Intracardiac Impedances with an Implantable Lead System," filed Mar. 31, 2006, and in U.S. patent application Ser. Nos. 11/558,101; 11/557,851; 11/557,870; 11/557,882; and Ser. No. 11/558,088, each entitled "Systems and Methods to Monitor and Treat Heart Failure Conditions," of Panescu et al. See, also, U.S. patent application Ser. No. 11/558,194, by Panescu et al., entitled "Closed-Loop Adaptive Adjustment of Pacing Therapy based on Cardiogenic Impedance Signals Detected by an Implantable Medical Device." Also, see, U.S. patent application Ser. Nos. 11/779,350 and 11/779,380 of Wenzel et al. filed Jul. 18, 2007, both entitled "System and Method for Estimating Cardiac Pressure based on Cardiac Electrical Conduction Delays Using an Implantable Medical Device." See, also, U.S. patent application Ser. No. 11/856,443, filed Sep. 17, 2007 of Zhao et al., entitled "MEMS-Based Left Atrial Pressure Sensor for Use with an Implantable Medical Device."

At step 702, the system subdivides or windows the LAP signal with the first third of the interval being systolic (ventricular) and the second two-thirds being the diastolic (atrial) and detects peak amplitudes in the windows. At step 704, the system then detects MR based on an analysis of the LAP signal (alone or in combination with an IEGM or surface EKG). At step 706, the system adjusts pacing parameters to optimize the area under the atrial portion of the curve to ensure that atrial kick is not truncated by a PVC and/or use timing of C-wave to determine closure of mitral valve and adjust AV delay to move C-wave to middle of X-descent to reduce size of A-wave and potentially lower LAP (see FIG. 14, discussed below.) At step 708, diagnostics are generated and recorded pertaining to the LAP-based optimization process and the LAP waveforms.

Note that at least some of these LAP-based applications might be performed using a PAP signal. However, the use of a PAP signal may be more difficult for these applications because of the physical separation of the pressure transducer placement providing a much reduced signal resolution (and potentially some LAP signal attenuation by time it is read in the PA.) In addition, the RV pressure in comparison is so much higher that it may be difficult to separate the two components. The LAP signal however has very distinct A, C, V (atrial contraction, valve closure, and mitral bulging from ventricular contraction) components, which can be advantageously exploited.

Figure 14:
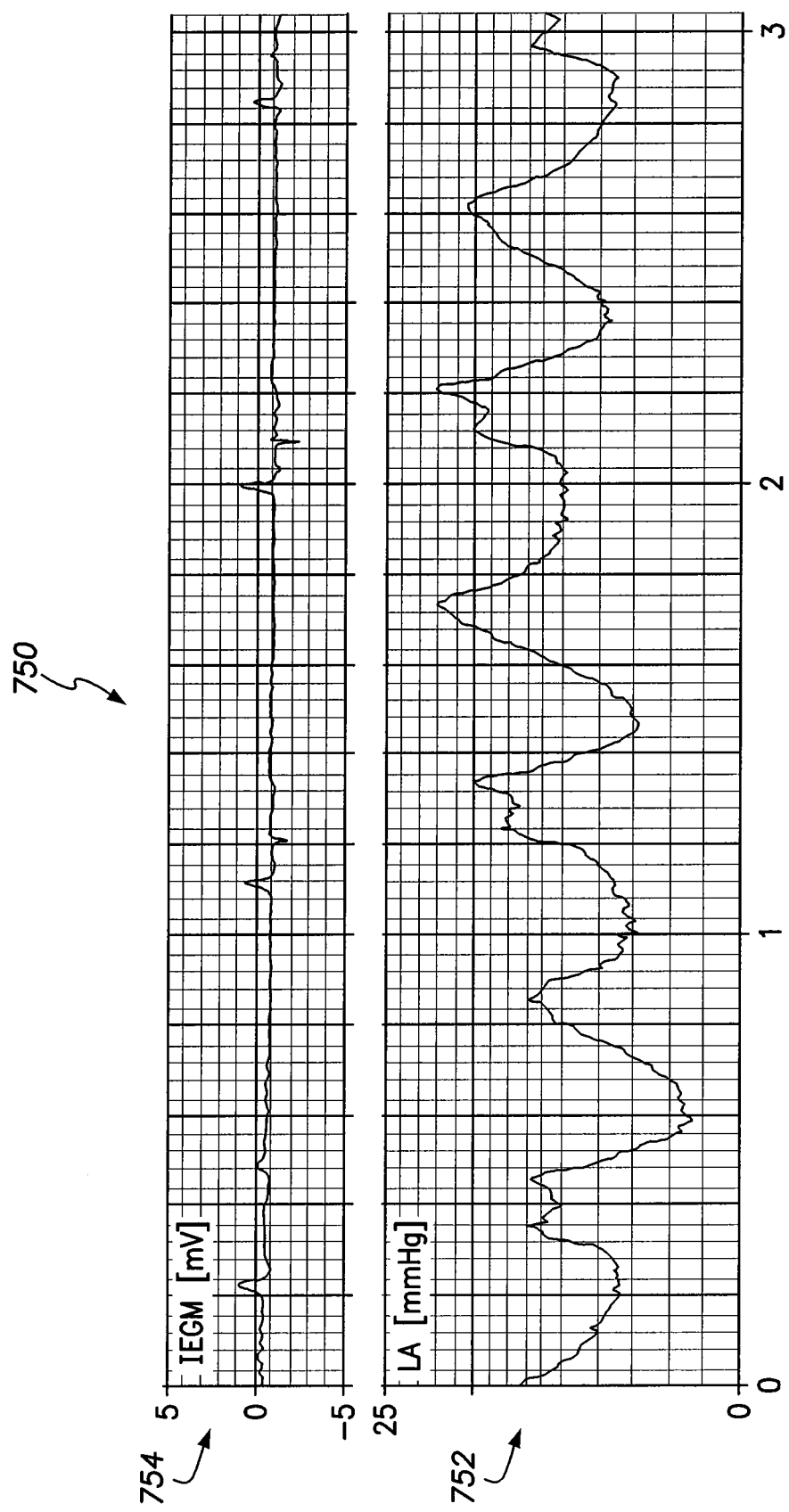
FIG. 14 is a graphic illustrating LAP and IEGM traces exploited by aspects of the exemplary LAP-based technique of FIG. 13.

FIG. 14 illustrates the example of step 706 of FIG. 13 wherein AV optimization may be achieved using A wave, V wave and C wave (closure of mitral valve) of an LAP waveform. In this example, the timing of timing of C wave (similar to dicrotic notch) can be used to determine closure of MV. As can be seen from LAP trace 752 of graph 750, the C-wave sits on the A-wave, indicating that the left atrium continues to contract while the mitral valve is closing and therefore only partially priming the LV. Lengthening the A-V delay to 170-200 msec may move the C-wave to the middle of the X-descent where it normally resides during sinus rhythm, thereby reducing the size of the a-wave and potentially further lowering LAP. Graph 750 also shows the corresponding IEGM 754. The vertical lines show an AV delay of 150 ms.

Note also that the various pacing parameter optimization techniques described herein may be performed in conjunction with other adjustment or optimization techniques (depending upon the capabilities of the system.) See, for example, the following patents and patent applications that set forth various systems and methods for determining and/or adjusting pacing delays or other pacing parameters: U.S. Pat. No. 7,590,446 of Min et al.; U.S. Published Application No. 2009/0299423 of Min; U.S. patent application Ser. No. 11/952,743, filed Dec. 7, 2007, entitled "Systems and Methods for Determining Optimal Atrio-Ventricular Pacing Delays using either Paced or Sensed Atrial Beats"; U.S. Published Application No. 2010/0145405, entitled "Systems and Methods for Controlling Ventricular Pacing in Patients with Long Intra-Atrial Conduction Delays"; U.S. Pat. No. 8,265,755, of Min et al. entitled "Systems and Methods for Optimizing Ventricular Pacing Delays for Use with Multi-Pole Leads"; U.S. Published Application No. 2011/0022112, of Min et al., entitled "Systems and Methods for Determining Ventricular Pacing Sites for use with Multi-Pole Leads"; U.S. Pat. No. 8,145,311, of Min et al., entitled "Systems and Methods for Determining Optimal Electrode Pairs for Use in Biventricular Pacing Using Multi-Pole Ventricular Leads"; U.S. Published Application No. 2012/0136406, of Min, entitled "Systems and Methods for Determining Optimal Atrioventricular Pacing Delays Based on Cardiomechanical Delays"; and U.S. Published Application No. 2012/0165892, of Min et al., entitled "Systems and Methods for Optimizing AV/VV Pacing Delays Using Combined IEGM/Impedance-based Techniques for Use with Implantable Medical Devices." See, also, U.S. Pat. No. 7,248,925, to Bruhns et al., entitled "System and Method for Determining Optimal Atrioventricular Delay based on Intrinsic Conduction Delays." See, also, U.S. patent application Ser. No. 13/023,408 of Min, filed Feb. 8, 2011, entitled "Systems and Methods for Tracking Stroke Volume Using Hybrid Impedance Configurations Employing a Multi-Pole Implantable Cardiac Lead." At least some of the techniques are implemented within the QuickOpt™ systems of St. Jude Medical.

For the sake of completeness, an exemplary CRMD will now be described for use with embodiments where the PAP monitor is a feature or component of the CRMD.

Exemplary CRMD with on-Board PAP Monitor

Figure 15:
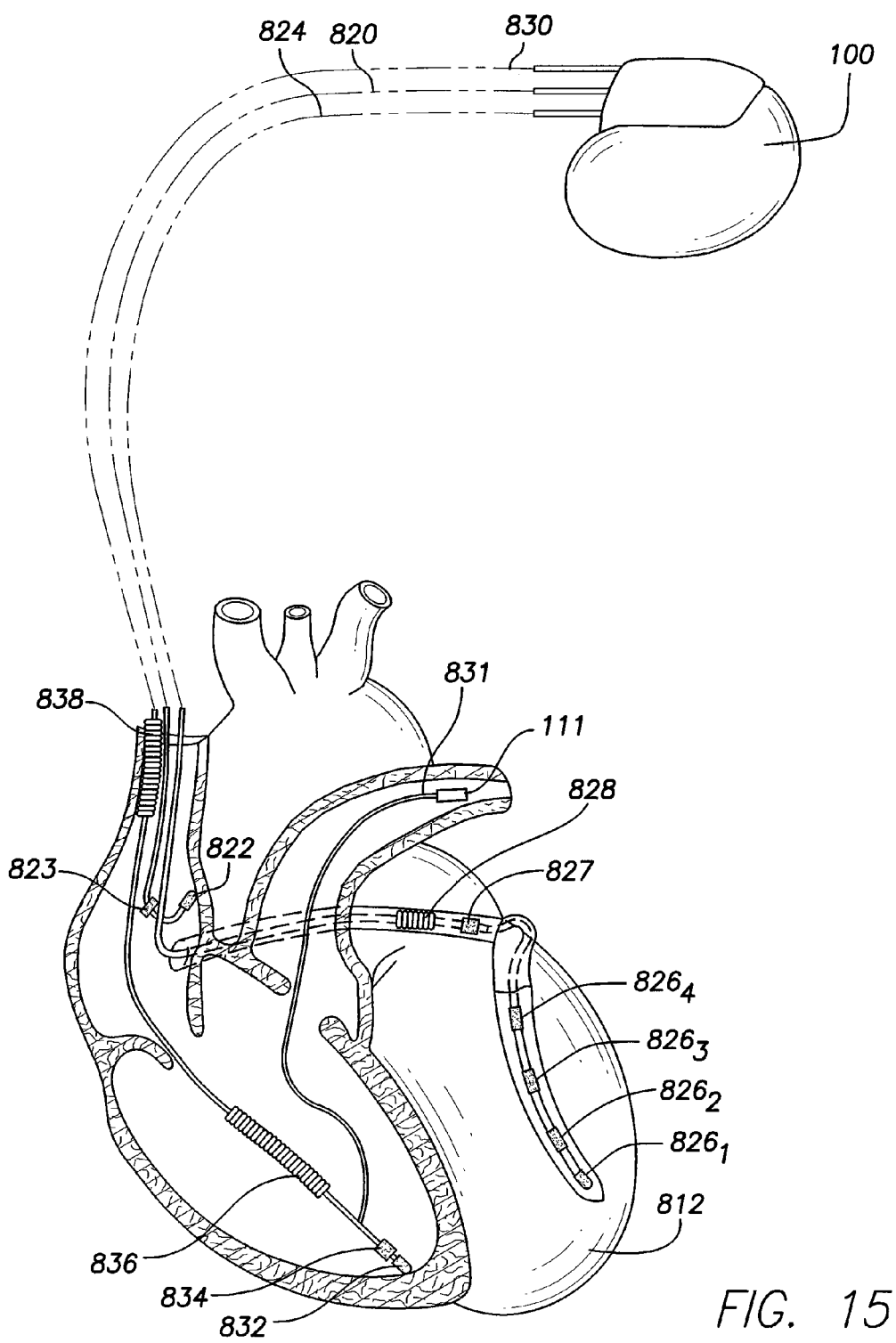
FIG. 15 is a simplified, partly cutaway view, illustrating the CRMD of FIG. 2 along with at set of leads implanted in or on the heart of the patient.
Figure 16:
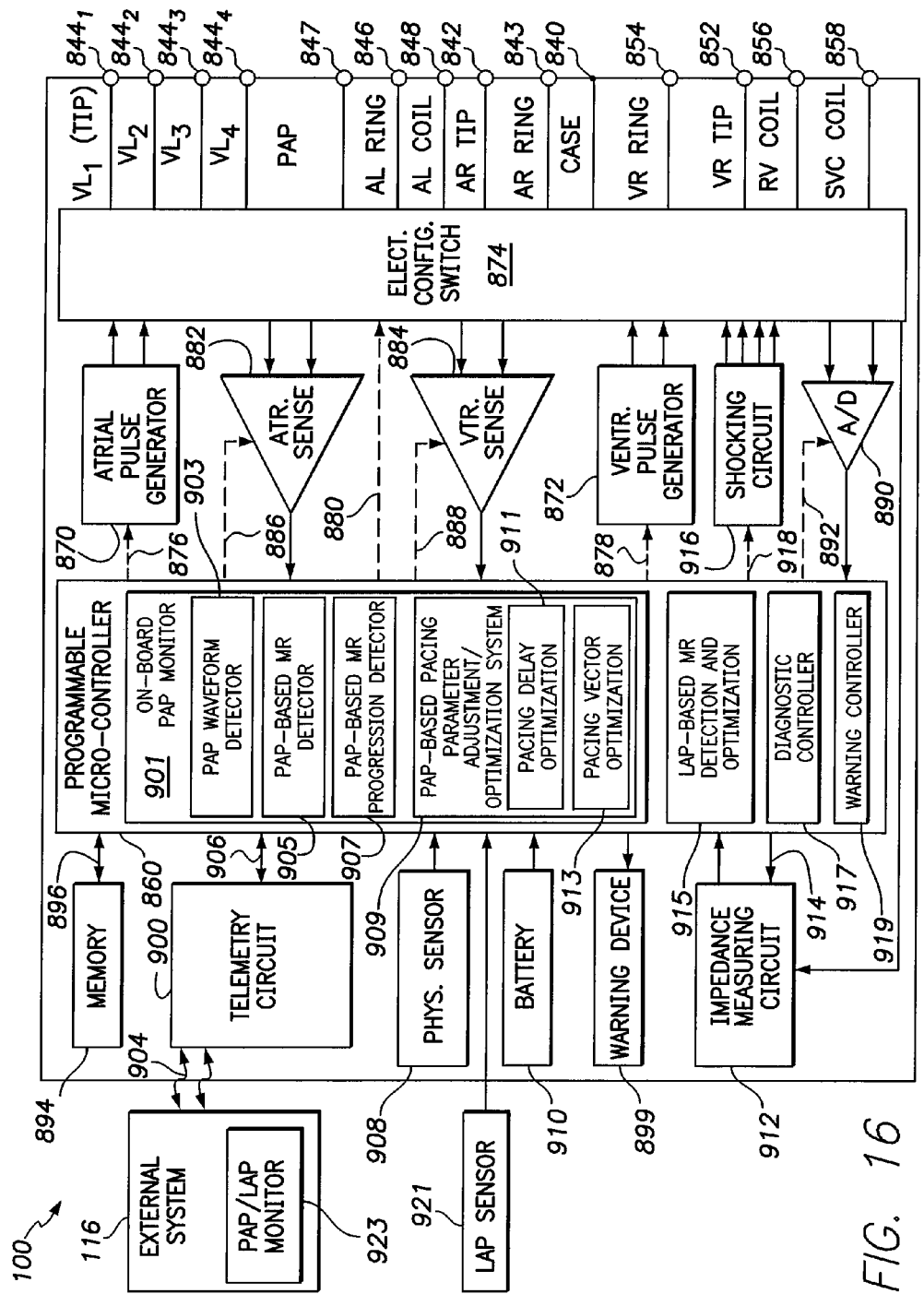
FIG. 16 is a functional block diagram of the CRMD of FIG. 15, illustrating basic circuit elements that provide cardioversion, defibrillation and/or pacing stimulation in the heart and particularly illustrating components of an on-board PAP monitor and PAP-based pacing optimization system.

With reference to FIGS. 15 and 16, an exemplary CRMD will now be described where the device is equipped with an on-board PAP monitor. FIG. 15 provides a simplified block diagram of the CRMD, which is a dual-chamber stimulation device capable of treating both fast and slow arrhythmias with stimulation therapy, including cardioversion, defibrillation and pacing stimulation, including CRT stimulation using a quad-pole LV lead. To provide atrial chamber pacing stimulation and sensing, CRMD 100 is in electrical communication with a heart 812 by way of a left atrial lead 820 having an atrial tip electrode 822 and an atrial ring electrode 823 implanted in the atrial appendage. CRMD 100 is also in electrical communication with the heart by way of a right ventricular lead 830 having, in this embodiment, a ventricular tip electrode 832, a right ventricular ring electrode 834, a right ventricular (RV) coil electrode 836, and a superior vena cava (SVC) coil electrode 838. The SVC coil electrode, as with many lead components, is optional. Typically, the right ventricular lead 830 is transvenously inserted into the heart so as to place the RV coil electrode 836 in the right ventricular apex, and the SVC coil electrode 838 in the superior vena cava. Accordingly, the right ventricular lead is capable of receiving cardiac signals, and delivering stimulation in the form of pacing and shock therapy to the right ventricle.

Right ventricular lead 830 also includes a pulmonary artery extension 831 equipped with a PA sensor 111. In one example, the pulmonary artery extension 831 is sized, shaped and configured to position the sensor in the pulmonary artery as shown. In other examples, it is located above the RV coil (and below the tricuspid valve.) Signals representative of PAP are routed back along pulmonary artery extension 831 to the main portion of lead 830 and then to the CRMD for processing. This is just one example of a PAP sensor arrangement. See, also, sensors described in U.S. patent application Ser. No. 11/927,026, filed Oct. 29, 2007, of Nabutovsky et al., entitled "Systems and Methods for Exploiting Venous Blood Oxygen Saturation in Combination with Hematocrit or other Sensor Parameters for use with an Implantable Medical Device."

To sense left atrial and ventricular cardiac signals and to provide left chamber pacing therapy, CRMD 100 is coupled to an LV lead 824 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV lead 824 is designed to receive atrial and ventricular cardiac signals and to deliver left ventricular pacing therapy using a set of four left ventricular electrodes $826_1$, $826_2$, $826_3$, and $826_4$ (thereby providing a quadrupole lead), left atrial pacing therapy using at least a left atrial ring electrode 827, and shocking therapy using at least a left atrial coil electrode 828 implanted on or near the left atrium. In other examples, more or fewer LV electrodes are provided. Although only three leads are shown in FIG. 15, it should also be understood that additional leads (with one or more pacing, sensing and/or shocking electrodes) might be used and/or additional electrodes might be provided on the leads already shown, such as additional electrodes on the RV lead. Note that, on present commercially-available hardware, there is often no separate electrode 827.

A simplified block diagram of internal components of CRMD 100 is shown in FIG. 15. While a particular CRMD is shown, this is for illustrative purposes only, and one of skill in the art could readily duplicate, eliminate or disable the appropriate circuitry in any desired combination to provide a device capable of treating the appropriate chamber (s) with cardioversion, defibrillation and pacing stimulation. The housing 840 for CRMD 100, shown schematically in FIG. 15, is often referred to as the "can", "case" or "case electrode" and may be programmably selected to act as the return electrode for all "unipolar" modes. The housing 840 may further be used as a return electrode alone or in combination with one or more of the coil electrodes, 828, 836 and 838, for shocking purposes. The housing 840 further includes a connector (not shown) having a plurality of terminals, 842, 843, $844_1$-$844_4$, 845, 846, 848, 852, 854, 856 and 858 (shown schematically and, for convenience, the names of the electrodes to which they are connected are shown next to the terminals). As such, to achieve right atrial sensing and pacing, the connector includes at least a right atrial tip terminal ($A_R$ TIP) 842 adapted for connection to the atrial tip electrode 822 and a right atrial ring ($A_R$ RING) electrode 843 adapted for connection to right atrial ring electrode 823. To achieve left chamber sensing and pacing, the connector includes, at least, left ventricular tip and ring terminals 844 and 845, respectively. Additionally, a PAP terminal 847 is provided for receiving signals from PAP sensor 111 (FIG. 2.) If a separate LAP sensor is provided, an additional terminal may be needed. Within the figure, an LAP sensor 921 is shown schematically.

The connector also includes a left atrial ring terminal ($A_L$ RING) 846 and a left atrial shocking terminal ($A_L$ COIL) 848, which are adapted for connection to the left atrial ring electrode 827 and the left atrial coil electrode 828, respectively. To support right chamber sensing, pacing and shocking, the connector further includes a right ventricular tip terminal ($V_R$ TIP) 852, a right ventricular ring terminal ($V_R$ RING) 854, a right ventricular shocking terminal (RV COIL) 856, and an SVC shocking terminal (SVC COIL) 858, which are adapted for connection to the RV tip electrode 832, right ventricular ring electrode 834, the $V_R$ coil electrode 836, and the SVC coil electrode 838, respectively.

At the core of CRMD 100 is a programmable microcontroller 860, which controls the various modes of stimulation therapy. As is well known in the art, the microcontroller 860 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 860 includes the ability to process or monitor input signals (data) as controlled by a program code stored in a designated block of memory. The details of the design and operation of the microcontroller 860 are not critical to the invention. Rather, any suitable microcontroller 860 may be used that carries out the functions described herein. The use of microprocessor-based control circuits for performing timing and data analysis functions are well known in the art.

As shown in FIG. 15, an atrial pulse generator 870 and a ventricular pulse generator 872 generate pacing stimulation pulses for delivery by the right atrial lead 820, the right ventricular lead 830, and/or the LV lead 824 via an electrode configuration switch 874. It is understood that in order to provide stimulation therapy in each of the four chambers of the heart, the atrial and ventricular pulse generators, 870 and 872, may include dedicated, independent pulse generators, multiplexed pulse generators or shared pulse generators. The pulse generators, 870 and 872, are controlled by the microcontroller 860 via appropriate control signals, 876 and 878, respectively, to trigger or inhibit the stimulation pulses.

The microcontroller 860 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 874 includes a plurality of switches for connecting the desired electrodes to the appropriate I/O circuits, thereby providing complete electrode programmability. Accordingly, the switch 874, in response to a control signal 880 from the microcontroller 860, determines the polarity of the stimulation pulses (e.g., unipolar, bipolar, combipolar, etc.) by selectively closing the appropriate combination of switches (not shown) as is known in the art. The switch also switches among the various LV electrodes.

Atrial sensing circuits 882 and ventricular sensing circuits 884 may also be selectively coupled to the right atrial lead 820, LV lead 824, and the right ventricular lead 830, through the switch 874 for detecting the presence of cardiac activity in each of the four chambers of the heart. Accordingly, the atrial (ATR. SENSE) and ventricular (VTR. SENSE) sensing circuits, 882 and 884, may include dedicated sense amplifiers, multiplexed amplifiers or shared amplifiers. The switch 874 determines the "sensing polarity" of the cardiac signal by selectively closing the appropriate switches, as is also known in the art. In this way, the clinician may program the sensing polarity independent of the stimulation polarity. Each sensing circuit, 882 and 884, preferably employs one or more low power, precision amplifiers with programmable gain and/or automatic gain control, bandpass filtering, and a threshold detection circuit, as known in the art, to selectively sense the cardiac signal of interest. The automatic gain control enables CRMD 100 to deal effectively with the difficult problem of sensing the low amplitude signal characteristics of atrial or ventricular fibrillation. The outputs of the atrial and ventricular sensing circuits, 882 and 884, are connected to the microcontroller 860 which, in turn, are able to trigger or inhibit the atrial and ventricular pulse generators, 870 and 872, respectively, in a demand fashion in response to the absence or presence of cardiac activity in the appropriate chambers of the heart.

For arrhythmia detection, CRMD 100 utilizes the atrial and ventricular sensing circuits, 882 and 884, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 860 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks). As already explained, various irregular cardiac rhythms can also be detected based on PAP or LAP signals and components for controlling those functions are described below.

Cardiac signals are also applied to the inputs of an analog-to-digital (A/D) data acquisition system 890. The data acquisition system 890 is configured to acquire the IEGM signals, convert the raw analog data into a digital signal, and store the digital signals for later processing and/or telemetric transmission to an external device 16. The data acquisition system 890 is coupled to the right atrial lead 820, the LV lead 824, and the right ventricular lead 830 through the switch 874 to sample cardiac signals across any pair of desired electrodes. The microcontroller 860 is further coupled to a memory 894 by a suitable data/address bus 896, wherein the programmable operating parameters used by the microcontroller 860 are stored and modified, as required, in order to customize the operation of CRMD 100 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable CRMD 100 may be non-invasively programmed into the memory 894 through a telemetry circuit 900 in telemetric communication with the external device 116, such as a programmer, transtelephonic transceiver or a diagnostic system analyzer. The telemetry circuit 900 is activated by the microcontroller by a control signal 906. The telemetry circuit 900 advantageously allows intracardiac electrograms and status information relating to the operation of CRMD 1000 (as contained in the microcontroller 860 or memory 894) to be sent to the external device 116 through an established communication link 904. CRMD 100 further includes an accelerometer or other physiologic sensor 908, commonly referred to as a "rate-responsive" sensor because it is typically used to adjust pacing stimulation rate according to the exercise state of the patient. However, the physiological sensor 908 may further be used to detect changes in cardiac output, changes in the physiological condition of the heart, or diurnal changes in activity (e.g., detecting sleep and wake states) and to detect arousal from sleep. Accordingly, the microcontroller 860 responds by adjusting the various pacing parameters (such as rate, AV delay, VV delay, etc.) at which the atrial and ventricular pulse generators, 870 and 872, generate stimulation pulses. While shown as being included within CRMD 100, it is to be understood that the physiologic sensor 908 may also be external to CRMD 100, yet still be implanted within or carried by the patient. A common type of rate responsive sensor is an activity sensor incorporating an accelerometer or a piezoelectric crystal, which is mounted within the housing 840 of CRMD 100. Other types of physiologic sensors are also known, for example, sensors that sense the oxygen content of blood, respiration rate and/or minute ventilation, pH of blood, ventricular gradient, contractility, mechanical dyssynchrony, electrical dyssynchrony, photoplethysmography (PPG), LAP, heart sounds, etc. It should be understood that multiple separate sensors can be provided and, depending upon the parameter to be detected, at least some of the sensors might be positioned external to the device housing.

The CRMD additionally includes a battery 910, which provides operating power to all of the circuits shown in FIG. 15. The battery 910 may vary depending on the capabilities of CRMD 100. If the system only provides low voltage therapy, a lithium iodine or lithium copper fluoride cell typically may be utilized. For CRMD 100, which employs shocking therapy, the battery 910 should be capable of operating at low current drains for long periods, and then be capable of providing high-current pulses (for capacitor charging) when the patient requires a shock pulse. The battery 910 should also have a predictable discharge characteristic so that elective replacement time can be detected. Accordingly, appropriate batteries are employed.

As further shown in FIG. 15, CRMD 100 has an impedance measuring circuit 912, enabled by the microcontroller 860 via a control signal 914. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; detecting the motion of heart valves; and detecting cardiogenic impedance for use in estimating LAP, etc. Impedance measuring circuit 912 is coupled to switch 874 so that any desired electrode may be used.

In the case where CRMD 100 is intended to operate as an ICD device, it detects the occurrence of an arrhythmia requiring a shock, and automatically applies an appropriate electrical shock therapy to the heart aimed at terminating the arrhythmia. To this end, the microcontroller 860 further controls a shocking circuit 916 by way of a control signal 918. The shocking circuit 916 generates shocking pulses of low (up to 0.5 joules), moderate (0.5-10 joules) or high energy (11 to 40 joules or more), as controlled by the microcontroller 860. Such shocking pulses are applied to the heart of the patient through at least two shocking electrodes, and as shown in this embodiment, selected from the left atrial coil electrode 828, the RV coil electrode 836, and/or the SVC coil electrode 838. The housing 840 may act as an active electrode in combination with the RV electrode 836, or as part of a split electrical vector using the SVC coil electrode 838 or the left atrial coil electrode 828 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 10-40 joules or more), delivered asynchronously (since R-waves may be too disorganized), and pertaining exclusively to the treatment of fibrillation. Accordingly, the microcontroller 860 is capable of controlling synchronous or asynchronous delivery of shocking pulses.

An internal warning device 899 may be provided for generating perceptible warning signals to the patient pertaining to MR or other issues. The warning signals are generated via vibration, voltage or other methods.

Insofar as PAP is concerned, the microcontroller includes an on-board PAP monitor 901 operative to perform or control the PAP monitoring functions described above. In this example, the PAP monitor includes: a PAP detector 903 operative to input PAP signals received from the PAP sensor and detect PAP waveforms within the PAP signal corresponding to cardiac cycles. A PAP-based MR detector 905 is operative to detect regurgitation peaks, if present, within the PAP waveforms and then detect MR in the patient based on the regurgitation peaks. A PAP-based MR progression detector 907 is operative to detect progression of MR based, for example, on increasing amplitude of MR peaks over time. A PAP-based pacing parameter adjustment/optimization system 909 adjusts or optimizes various pacing parameters such as pacing delays and pacing vector selection based on the PAP signals, alone or in combination with IEGM signals, as described above. As shown, PAP-based pacing parameter adjustment/optimization system 909 may include a pacing delay optimization system 911 for optimizing AV, VV and LV inter-electrode delays and a pacing vector optimization system 913 for optimizing the selection of pacing vectors or related parameters. Additionally, if the CRMD is equipped to sense time-varying LAP signals (or proxies for LAP), the CRMD may be provided with an LAP-based MR detection and optimization system 915 operative to perform the LAP-based detection and optimization techniques described above. A diagnostic controller 917 controls the generation and recordation of diagnostics pertaining to PAP or LAP, MR or other matters. Warnings or alerts may be generated under the control of warning controller 919.

Depending upon the implementation, the various components of the microcontroller may be implemented as separate software modules or the modules may be combined to permit a single module to perform multiple functions. Although shown as components of the microcontroller, some or all of the components may be implemented separately from the microcontroller, using application specific integrated circuits (ASICs) or the like. As already explained, some or all of the techniques described herein can be performed by (or under the control of) an external device such as an external PAP monitor. Within FIG. 16, external system 116 is shown as including a PAP/LAP monitor 923, which may include components corresponding to blocks 901-919.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use with an implantable pulmonary artery pressure sensor and an implantable cardiac rhythm management device (CRMD) for implant within a patient, the method comprising:
sensing a pulmonary artery pressure (PAP) signal representative of variations in PAP occurring during individual cardiac cycles within the patient;
detecting a rate of change of the PAP signal with time (dPAP/dt);
detecting a maximum in the dPAP/dt signal (dPAP/dt|max) and a minimum in the dPAP/dt signal (dPAP/dt|min) within a portion of the PAP signal corresponding to an individual cardiac cycle; and
examining the dPAP/dt signal within a window between dPAP/dt|max and dPAP/dt|min to detect regurgitation peaks, if present, within the PAP signal;
detecting mitral regurgitation (MR) based on the presence of a regurgitation peak in the PAP signal;
detecting a pulmonary artery systole (PAS) peak within the PAP signal corresponding to a cardiac cycle;
detecting a delay interval between the PAS peak and the regurgitation peak; and
adjusting a cardiac pacing parameter based, at least in part, on the delay interval.

2. The method of claim 1 wherein detecting MR in the patient based on presence of regurgitation peaks in the PAP signal includes generating an indication of MR if MR peaks are detected in the PAP signal.

3. The method of claim 2 further including detecting progression of MR in the patient based on changes, if any, in the MR peaks over time.

4. The method of claim 1 wherein adjusting a cardiac pacing parameter includes adjusting an atrioventricular (AV) pacing delay.

5. The method of claim 4 wherein adjusting a cardiac pacing parameters additionally includes adjusting an interventricular (VV) pacing delay.

6. The method of claim 5 including performing further adjustments to pacing parameters based a hemodynamic optimization during a period of time when a pulmonary vascular resistance (PVR) value is substantially constant within the patient.

7. The method of claim 6 wherein the hemodynamic optimization includes:
estimating a value proportional to cardiac output (CO) from the PAP signal while PVR is substantially constant within the patient; and
adjusting a pacing parameter to improve CO.

8. The method of claim 7 wherein adjusting a pacing parameter to improve CO includes:
determining maximum values for PAP (maxPAP) within the PAP signal corresponding to a plurality of cardiac cycles;
determining a mean of the maxPAP values (maxPAP|mean);
determining a pulmonary artery diastole (PAD) pressure within a portion of the PAP signal corresponding to a current cardiac cycle;
determining a difference between maxPAP|mean and PAD pressure and comparing the difference between maxPAP|mean and PAD pressure against a threshold indicative of sufficient CO;
if the difference between maxPAP|mean and PAD pressure is less than the threshold indicative of sufficient CO, adjusting the pacing parameter to increase CO; and
if the difference between maxPAP|mean and PAD pressure is greater than or equal to the threshold indicative of sufficient CO indicating that the current pacing parameters are sufficiently optimized for further pacing.

9. The method of claim 7 wherein the CRMD is equipped for cardiac resynchronization therapy (CRT) using a selectable set of pacing vectors and the pacing parameter optimized based on CO specifies one or more pacing vectors.

10. The method of claim 1 including performing a further adjustment of pacing parameters based on an assessment of the filling and emptying of the right ventricle (RV) and left atrium (LA) of the heart of the patient.

11. The method of claim 10 wherein assessing the filling and emptying of the RV and LA of the heart of the patient includes:
dividing a PAP waveform corresponding to a cardiac cycle into an RV systolic emptying portion and an LA diastolic filling portion by detecting a dicrotic notch within the PAP waveform;
detecting morphological parameters representative of the RV systolic emptying portion and the LA diastolic filling portion of the PAP waveform; and
adjusting a pacing parameter to improve hemodynamics based on the morphological parameters representative of the RV systolic emptying portion and the LA diastolic filling portion of the PAP waveform.

12. The method of claim 11 wherein the morphological parameters include one or more of the slope, interval duration and area under the curve of the PAP waveform within the RV systolic emptying and the LA diastolic filling portions of the PAP waveform.

13. The method of claim 1 further including:
sensing a left atrial pressure (LAP) signal representative of variations in LAP during individual heart beats; and
detecting MR based, in part, on the LAP signal.

14. The method of claim 13 for use with an implantable cardiac rhythm management device (CRMD) and further including:
adjusting one or more pacing delays based, in part, on the LAP signal.

15. The method of claim 1 wherein at least some of the steps are performed by an external system that receives PAP signals from the implantable PAP sensor.

16. The method of claim 1 wherein at least some of the steps are performed by an implantable cardiac rhythm management device (CRMD) that receives PAP signals from the implantable PAP sensor.

17. A method for use with an implantable pulmonary artery pressure sensor and an implantable cardiac rhythm management device (CRMD) for implant within a patient, the method comprising:
sensing a pulmonary artery pressure (PAP) signal representative of variations in PAP occurring during individual cardiac cycles within the patient;
detecting closure of AV valves within a portion of the PAP signal corresponding to a cardiac cycle;
detecting a ventricular depolarization event (R-wave) within an electrical cardiac signal corresponding to the same cardiac cycle subsequent to the detected closure of the AV valves;
detecting a delay interval (DeltaTime1) between the closure of AV valves and the R-wave detected subsequent to the detected closure of the AV valve; and
adjusting an AV delay based on the delay interval (DeltaTime1).

18. The method of claim 17 wherein the electrical cardiac cycle is one or more of an intracardiac electrogram (IEGM) and a surface electrocardiogram (EKG).

19. The method of claim 17 wherein adjusting the AV pacing delay based on the delay interval (DeltaTime1) includes:
delivering pacing using a current value of the AV pacing delay;
determining whether the closure of AV valves occurs before the R-wave by an amount sufficient so that delay interval (DeltaTime1) is acceptable;
if the closure of AV valves does not occur before the R-wave by an amount sufficient so that DeltaTime1 is acceptable, then adjusting the AV delay; and
if the closure of AV valves does occur before the R-wave by an amount sufficient so that DeltaTime1 is acceptable, then indicating that the current value of the AV pacing delay is sufficiently optimized for further pacing.

20. A method for use with an implantable pulmonary artery pressure sensor and an implantable cardiac rhythm management device (CRMD) for implant within a patient, the method comprising:
sensing a pulmonary artery pressure (PAP) signal representative of variations in PAP occurring during individual cardiac cycles within the patient;
detecting a pulmonary artery systole (PAS) peak within the PAP signal corresponding to a cardiac cycle;
detecting an MR peak within the PAP signal corresponding to the same cardiac cycle;
detecting a second delay interval (DeltaTime2) between the PAS peak and the MR peak; and
adjusting an interventricular (VV) pacing delay based on the second delay interval (DeltaTime2).

21. The method of claim 20 wherein adjusting the VV pacing delay based on the second delay interval (DeltaTime2) includes:
delivering pacing using a current value of the AV delay and a current value of the VV pacing delay;
determining whether the second delay interval (DeltaTime2) is acceptable;
if DeltaTime2 is not acceptable, adjusting the VV pacing delay; and
if DeltaTime2 is acceptable, then indicating that the current value of the VV pacing delay is sufficiently optimized for further pacing.

22. A system for use with an implantable pulmonary artery pressure sensor for implant within a patient, the system comprising:
means for sensing a pulmonary artery pressure (PAP) signal representative of variations in PAP occurring during cardiac cycles of the patient;
means for detecting a rate of change of the PAP signal with time (dPAP/dt), detecting a maximum in the dPAP/dt signal (dPAP/dt|max) and a minimum in the dPAP/dt signal (dPAP/dt|min) within a portion of the PAP signal corresponding to an individual cardiac cycle and examining the dPAP/dt signal within a window between dPAP/dt|max and dPAP/dt|min to detect;
means for detecting a regurgitation peak, if present, within the PAP signal;
means for detecting mitral regurgitation (MR) in the patient based on the MR peaks in the PAP signal;
means for detecting a pulmonary artery systole (PAS) peak within the PAP signal corresponding to a cardiac cycle;
means for detecting a delay interval between the PAS peak and the regurgitation peak; and
means for adjusting a cardiac pacing parameter based, at least in part, on the delay interval.

* * * * *